US012758363B2

(12) United States Patent
Derakhshan et al.

(10) Patent No.: US 12,758,363 B2
(45) Date of Patent: Oct. 13, 2026

(54) ACTIVATION OF EXISTING ATTACHMENTS IN ORTHODONTIC TREATMENT

(71) Applicant: Align Technology, Inc., San Jose, CA (US)

(72) Inventors: Mitra Derakhshan, Herndon, VA (US); Jun Sato, San Jose, CA (US); Crystal Tjhia, Sunnyvale, CA (US); Bastien Pesenti, San Jose, CA (US); Jessica H. Schiltz, San Jose, CA (US); Palak Mittal, Sunnyvale, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 19/242,887

(22) Filed: Jun. 18, 2025

(65) Prior Publication Data

US 2025/0381011 A1 Dec. 18, 2025

Related U.S. Application Data

(60) Provisional application No. 63/661,537, filed on Jun. 18, 2024.

(51) Int. Cl.
*A61C 7/00* (2006.01)
*G16H 20/30* (2018.01)

(52) U.S. Cl.
CPC ............. *A61C 7/002* (2013.01); *G16H 20/30* (2018.01)

(58) Field of Classification Search
CPC ................................ A61C 7/002; G16H 20/30
USPC ............................................................ 433/24
See application file for complete search history.

(56) References Cited

U.S. PATENT DOCUMENTS

| | | | |
|---|---|---|---|
| 5,975,893 | A | 11/1999 | Chishti et al. |
| 6,227,850 | B1 | 5/2001 | Chishti et al. |
| 6,227,851 | B1 | 5/2001 | Chishti et al. |
| 6,299,440 | B1 | 10/2001 | Phan et al. |
| 6,318,994 | B1 | 11/2001 | Chishti et al. |
| 6,371,761 | B1 | 4/2002 | Cheang et al. |
| 6,386,878 | B1 | 5/2002 | Pavlovskaia et al. |
| 6,406,292 | B1 | 6/2002 | Chishti et al. |
| 6,409,504 | B1 | 6/2002 | Jones et al. |
| 6,457,972 | B1 | 10/2002 | Chishti et al. |
| 6,488,499 | B1 | 12/2002 | Miller |
| 6,514,074 | B1 | 2/2003 | Chishti et al. |
| 6,554,611 | B2 | 4/2003 | Chishti et al. |
| 6,582,229 | B1 | 6/2003 | Miller et al. |
| 6,602,070 | B2 | 8/2003 | Miller et al. |

(Continued)

*Primary Examiner* — Sunil K Singh
(74) *Attorney, Agent, or Firm* — Shay Glenn LLP

(57) ABSTRACT

Methods and apparatuses for orthodontic treatment planning, including determining whether and how to activate existing attachments for use in secondary treatment. In some cases, activation may be by the dental appliance rather than through the attachment object. The secondary treatment may be needed to further treat the patient's teeth. The existing attachments may have been used as part of a previous treatment plan. A scan of the patient's teeth with the attachments is used as a basis to determine whether the existing attachments have a suitable shape and/or other characteristics for activation. If one or more of the existing attachments is determined to be suitable for activation, a secondary treatment plan can be generated based on activation of the existing attachments.

20 Claims, 12 Drawing Sheets

(56) References Cited

U.S. PATENT DOCUMENTS

| | | | |
|---|---|---|---|
| 6,621,491 | B1 | 9/2003 | Baumrind et al. |
| 6,688,886 | B2 | 2/2004 | Hughes et al. |
| 6,726,478 | B1 | 4/2004 | Isiderio et al. |
| 6,729,876 | B2 | 5/2004 | Chishti et al. |
| 6,739,869 | B1 | 5/2004 | Taub et al. |
| 6,767,208 | B2 | 7/2004 | Kaza |
| 6,783,360 | B2 | 8/2004 | Chishti |
| 7,040,896 | B2 | 5/2006 | Pavlovskaia et al. |
| 7,063,532 | B1 | 6/2006 | Jones et al. |
| 7,074,038 | B1 | 7/2006 | Miller |
| 7,074,039 | B2 | 7/2006 | Kopelman et al. |
| 7,077,647 | B2 | 7/2006 | Choi et al. |
| 7,108,508 | B2 | 9/2006 | Hedge et al. |
| 7,134,874 | B2 | 11/2006 | Chishti et al. |
| 7,156,661 | B2 | 1/2007 | Choi et al. |
| 7,160,107 | B2 | 1/2007 | Kopelman et al. |
| 7,241,142 | B2 | 7/2007 | Abolfathi et al. |
| 7,293,988 | B2 | 11/2007 | Wen |
| 7,357,634 | B2 | 4/2008 | Knopp |
| 7,555,403 | B2 | 6/2009 | Kopelman et al. |
| 7,637,740 | B2 | 12/2009 | Knopp |
| 7,689,398 | B2 | 3/2010 | Cheng et al. |
| 7,736,147 | B2 | 6/2010 | Kaza et al. |
| 7,746,339 | B2 | 6/2010 | Matov et al. |
| 7,844,356 | B2 | 11/2010 | Matov et al. |
| 7,844,429 | B2 | 11/2010 | Matov et al. |
| 7,865,259 | B2 | 1/2011 | Kuo et al. |
| 7,878,804 | B2 | 2/2011 | Korytov et al. |
| 7,880,751 | B2 | 2/2011 | Kuo et al. |
| 7,904,308 | B2 | 3/2011 | Arnone et al. |
| 7,930,189 | B2 | 4/2011 | Kuo |
| 7,942,672 | B2 | 5/2011 | Kuo |
| 7,970,627 | B2 | 6/2011 | Kuo et al. |
| 7,970,628 | B2 * | 6/2011 | Kuo ...................... G16H 50/70 705/2 |
| 8,038,444 | B2 | 10/2011 | Kitching et al. |
| 8,044,954 | B2 | 10/2011 | Kitching et al. |
| 8,075,306 | B2 | 12/2011 | Kitching et al. |
| 8,092,215 | B2 | 1/2012 | Stone-Collonge et al. |
| 8,099,268 | B2 | 1/2012 | Kitching et al. |
| 8,108,189 | B2 | 1/2012 | Chelnokov et al. |
| 8,126,726 | B2 | 2/2012 | Matov et al. |
| 8,260,591 | B2 | 9/2012 | Kass et al. |
| 8,275,180 | B2 | 9/2012 | Kuo |
| 8,401,826 | B2 | 3/2013 | Cheng et al. |
| 8,439,672 | B2 | 5/2013 | Matov et al. |
| 8,562,338 | B2 | 10/2013 | Kitching et al. |
| 8,591,225 | B2 | 11/2013 | Wu et al. |
| 8,788,285 | B2 | 7/2014 | Kuo |
| 8,843,381 | B2 | 9/2014 | Kuo et al. |
| 8,874,452 | B2 | 10/2014 | Kuo |
| 8,896,592 | B2 | 11/2014 | Boltunov et al. |
| 8,930,219 | B2 | 1/2015 | Trosien et al. |
| 9,037,439 | B2 | 5/2015 | Kuo et al. |
| 9,060,829 | B2 | 6/2015 | Sterental et al. |
| 9,125,709 | B2 | 9/2015 | Matty |
| 9,211,166 | B2 | 12/2015 | Kuo et al. |
| 9,220,580 | B2 | 12/2015 | Borovinskih et al. |
| 9,364,296 | B2 | 6/2016 | Kuo |
| 9,375,300 | B2 | 6/2016 | Matov et al. |
| 9,414,897 | B2 | 8/2016 | Wu et al. |
| 9,492,245 | B2 | 11/2016 | Sherwood et al. |
| 9,642,678 | B2 | 5/2017 | Kuo |
| 10,248,883 | B2 | 4/2019 | Borovinskih et al. |
| 10,342,638 | B2 | 7/2019 | Kitching et al. |
| 10,463,452 | B2 | 11/2019 | Matov et al. |
| 10,595,966 | B2 | 3/2020 | Carrier, Jr. et al. |
| 10,617,489 | B2 | 4/2020 | Grove et al. |
| 10,722,328 | B2 | 7/2020 | Velazquez et al. |
| 10,779,718 | B2 | 9/2020 | Meyer et al. |
| 10,792,127 | B2 | 10/2020 | Kopelman et al. |
| 10,835,349 | B2 | 11/2020 | Cramer et al. |
| 10,973,611 | B2 | 4/2021 | Pokotilov et al. |
| 10,996,813 | B2 | 5/2021 | Makarenkova et al. |
| 10,997,727 | B2 | 5/2021 | Xue et al. |
| 11,020,205 | B2 | 6/2021 | Li et al. |
| 11,020,206 | B2 | 6/2021 | Shi et al. |
| 11,026,766 | B2 | 6/2021 | Chekh et al. |
| 11,033,359 | B2 | 6/2021 | Velazquez et al. |
| 11,071,608 | B2 | 7/2021 | Derakhshan et al. |
| 11,096,863 | B2 | 8/2021 | Kajihara et al. |
| 11,116,605 | B2 | 9/2021 | Nyukhtikov et al. |
| 11,147,652 | B2 | 10/2021 | Mason et al. |
| 11,151,753 | B2 | 10/2021 | Gao et al. |
| 11,154,381 | B2 | 10/2021 | Roschin et al. |
| 11,259,896 | B2 | 3/2022 | Matov et al. |
| 11,357,598 | B2 | 6/2022 | Cramer |
| 11,395,717 | B2 | 7/2022 | Yuryev et al. |
| 11,432,908 | B2 | 9/2022 | Kopelman et al. |
| 11,464,604 | B2 | 10/2022 | Makarenkova et al. |
| 11,478,334 | B2 | 10/2022 | Matov et al. |
| 11,484,389 | B2 | 11/2022 | Sterental et al. |
| 11,534,272 | B2 | 12/2022 | Li et al. |
| 11,553,988 | B2 | 1/2023 | Mednikov et al. |
| 11,633,268 | B2 | 4/2023 | Moalem et al. |
| 11,642,195 | B2 | 5/2023 | Gao et al. |
| 11,651,494 | B2 | 5/2023 | Comito et al. |
| 11,654,001 | B2 | 5/2023 | Roschin et al. |
| 11,707,344 | B2 | 7/2023 | Roschin et al. |
| 11,723,748 | B2 | 8/2023 | Li et al. |
| 11,810,271 | B2 | 11/2023 | Shi et al. |
| 11,850,111 | B2 | 12/2023 | Derakhshan et al. |
| 11,864,970 | B2 | 1/2024 | Shojaei et al. |
| 11,903,793 | B2 | 2/2024 | Cramer et al. |
| 11,978,547 | B2 | 5/2024 | Levin et al. |
| 12,023,216 | B2 | 7/2024 | Pimenov et al. |
| 12,048,604 | B2 | 7/2024 | Roschin et al. |
| 12,048,605 | B2 | 7/2024 | Farkash et al. |
| 12,076,207 | B2 | 9/2024 | Liu et al. |
| 12,090,020 | B2 | 9/2024 | Cramer |
| 12,106,845 | B2 | 10/2024 | Meyer et al. |
| 12,109,088 | B2 * | 10/2024 | Salah ..................... A61C 9/004 |
| 12,125,581 | B2 | 10/2024 | Slynko et al. |
| 12,156,714 | B2 * | 12/2024 | Sato ..................... A61C 9/0053 |
| 12,193,905 | B2 | 1/2025 | Chekhonin et al. |
| 12,220,288 | B2 | 2/2025 | Chekh et al. |
| 12,370,016 | B2 | 7/2025 | Paraketsov et al. |
| 12,446,994 | B2 * | 10/2025 | Salah ................... A61C 9/0046 |
| 12,483,777 | B2 | 11/2025 | Cramer et al. |
| 2003/0008259 | A1 | 1/2003 | Kuo et al. |
| 2003/0143509 | A1 | 7/2003 | Kopelman et al. |
| 2003/0207227 | A1 | 11/2003 | Abolfathi |
| 2004/0137400 | A1 | 7/2004 | Chishti et al. |
| 2004/0152036 | A1 | 8/2004 | Abolfathi |
| 2004/0197728 | A1 | 10/2004 | Abolfathi et al. |
| 2004/0259049 | A1 | 12/2004 | Kopelman et al. |
| 2005/0182654 | A1 | 8/2005 | Abolfathi et al. |
| 2005/0244791 | A1 | 11/2005 | Davis et al. |
| 2006/0127836 | A1 | 6/2006 | Wen |
| 2006/0127852 | A1 | 6/2006 | Wen |
| 2006/0127854 | A1 | 6/2006 | Wen |
| 2006/0275731 | A1 | 12/2006 | Wen et al. |
| 2006/0275736 | A1 | 12/2006 | Wen et al. |
| 2008/0306724 | A1 | 12/2008 | Kitching et al. |
| 2010/0009308 | A1 | 1/2010 | Wen et al. |
| 2010/0068672 | A1 | 3/2010 | Arjomand et al. |
| 2010/0068676 | A1 | 3/2010 | Mason et al. |
| 2010/0092907 | A1 | 4/2010 | Knopp |
| 2010/0138025 | A1 * | 6/2010 | Morton ................... G06F 17/10 700/103 |
| 2010/0167243 | A1 | 7/2010 | Spiridonov et al. |
| 2013/0204599 | A1 | 8/2013 | Matov et al. |
| 2017/0273760 | A1 | 9/2017 | Morton et al. |
| 2022/0104920 | A1 | 4/2022 | Wang et al. |
| 2022/0165388 | A1 | 5/2022 | Chernov et al. |
| 2022/0262007 | A1 | 8/2022 | Cramer et al. |
| 2022/0378549 | A1 | 12/2022 | Blanco et al. |
| 2023/0008836 | A1 | 1/2023 | Yazykov et al. |
| 2023/0056427 | A1 | 2/2023 | Blanco et al. |
| 2023/0190411 | A1 | 6/2023 | Chiu et al. |
| 2023/0225831 | A1 | 7/2023 | Cramer et al. |
| 2023/0263594 | A1 | 8/2023 | Lobsiger et al. |
| 2023/0301752 | A1 | 9/2023 | Wang et al. |
| 2023/0325558 | A1 | 10/2023 | Kukk et al. |

(56) References Cited

U.S. PATENT DOCUMENTS

| | | | |
|---|---|---|---|
| 2023/0352150 | A1 | 11/2023 | Meyer et al. |
| 2023/0414323 | A1 | 12/2023 | Sun et al. |
| 2024/0033041 | A1 | 2/2024 | Chernov et al. |
| 2024/0033045 | A1 | 2/2024 | Tanugula et al. |
| 2024/0065807 | A1 | 2/2024 | Chang et al. |
| 2024/0087184 | A1 | 3/2024 | Gao et al. |
| 2024/0108436 | A1 | 4/2024 | Grebenkin et al. |
| 2024/0122463 | A1 | 4/2024 | Li et al. |
| 2024/0122677 | A1 | 4/2024 | Popov et al. |
| 2024/0131795 | A1 | 4/2024 | Li et al. |
| 2024/0144480 | A1 | 5/2024 | Seeber et al. |
| 2024/0177397 | A1 | 5/2024 | Li et al. |
| 2024/0185420 | A1 | 6/2024 | Cramer et al. |
| 2024/0185518 | A1 | 6/2024 | Seeber et al. |
| 2024/0189078 | A1 | 6/2024 | Cramer et al. |
| 2024/0197449 | A1 | 6/2024 | Stroganov et al. |
| 2024/0216106 | A1 | 7/2024 | Choi et al. |
| 2024/0257342 | A1 | 8/2024 | Semenov et al. |
| 2024/0277450 | A1 | 8/2024 | Sherstennikov et al. |
| 2024/0293200 | A1 | 9/2024 | Kirsanov et al. |

* cited by examiner

ACTIVATION OF EXISTING ATTACHMENTS IN ORTHODONTIC TREATMENT

CLAIM OF PRIORITY

This patent application claims priority to U.S. Provisional Patent Application No. 63/661,537, titled "ACTIVATION OF EXISTING ATTACHMENTS IN ORTHODONTIC TREATMENT," and filed on Jun. 18, 2024, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Orthodontics is a dental specialty in which a patient's teeth are moved to positions where function and/or aesthetics are optimized. In some cases, the treatment involves the use of removable dental appliances that are designed to apply force on the patient's teeth and to gradually urge the teeth toward their intended positions according to a dental treatment plan. In some instances, the dental appliances may be configured to apply forces to the patient's teeth through one or more dental attachments bonded to the patient's teeth. The dental attachments have surfaces that are arranged to engage with dental appliances, and the dental appliance have surfaces configured to engage with the dental attachments, so that the appropriate forces can be applied through the attachments and onto the teeth.

In some cases, the clinician may determine that tooth movement of the patient has progressed as much as expected, or that further tooth movement is desired. This may be determined after a treatment plan has been completed or before treatment has been completed (e.g. mid-course). In such cases, a secondary treatment plan may be implemented to make any adjustments or corrections to the tooth positions. The changes may require minor refinements or major movements of the teeth to achieve a desired outcome. To implement the secondary treatment plan, the clinician may need to remove one or more of the already bonded attachments from the patient's teeth. Removing attachments from a patient's teeth is time consuming for the clinician and the patient. In addition, in some cases the existing attachments may be perfectly fine for active use in the secondary treatment plan. However, current orthodontic techniques and systems do not provide a way to determine whether the existing attachments can be actively used (e.g., to apply a controlled orthodontic force) in the secondary treatment plan or provide a way to implement them in the secondary treatment plan.

It would be particularly beneficial to provide techniques and orthodontic systems to make orthodontic treatment planning simpler and more flexible for dental practitioners. It would also be beneficial to provide techniques and orthodontic systems for using existing attachments to improve the efficiency of treatment planning when changes or refinements to the treatment plan are necessary.

SUMMARY OF THE DISCLOSURE

The present disclosure generally relates to orthodontic treatments and the use of dental attachments. More particularly, the present disclosure is related to systems, devices, and methods for treatment planning for activating dental attachments that already exist on a patient's teeth, as well as fabrication of dental appliances.

Described herein are methods and apparatuses (e.g., systems, devices, software) for treatment planning including using attachments (e.g., composite dental attachments) that are already on a patient's teeth. One or more images (e.g., a scan) of the patient's teeth, with the attachments on the teeth, are analyzed to determine whether attachments should be removed from the teeth, used as a 'passive' attachment, or used as an 'active' attachment as part of a secondary treatment plan. Active attachments are attachments that are configured to actively engage with a dental appliance to apply planned repositioning forces on the teeth. Passive attachments are attachments that are on the patient's teeth but are not configured to actively engage with a dental appliance to apply planned repositioning forces on the teeth.

Benefits of this solution may include enhancing the biomechanical efficacy of treatment and increasing the efficiency of the dental professional. Attachment bonding procedures may be targeted for potentially a smaller subset of cases that require re-bonding of new attachments for a secondary treatment.

In general, orthodontic treatment planning may include the collection and processing of images of the patient's teeth. These images may be used to determine the current configuration of the patient's teeth and as a basis for determining a final tooth configuration representing a desired final outcome. Treatment planning software may be used to generate a treatment plan in which the teeth are incrementally moved over multiple stages, with each stage typically associated with a corresponding dental appliance (e.g., aligner). In some cases, the dental appliance is configured to apply forces to the patient's teeth via dental attachments bonded to the patient's teeth.

A secondary treatment plan refers to a treatment plan for orthodontically treating a subject's teeth after a previous treatment plan, or a portion of the previous treatment plan, has been completed. The secondary treatment plan may be based on digital three-dimensional (3D) models of the subject's dentition. For example, an initial model may represent the subject's dentition prior to the secondary treatment, a target or final model may represent the subject's dentition when secondary treatment is complete, and one or more intermediate models may represent the subject's dentition at one or more intermediate stages of the secondary treatment plan.

For example, described herein are methods for secondary orthodontic treatment planning, the method comprising: receiving a scan of a subject's dentition including an existing attachment on the subject's dentition; determining a shape of the existing attachment based on comparing the scan to one or more prior scans of the subject's dentition; determining that the existing attachment is suitable for activation to achieve one or more tooth movements, at least partially based on the shape of the existing attachment; identify a dental appliance engagement surface of the existing attachment when the attachment is suitable for activation; generating the secondary treatment plan including applying a force to the subject's dentition via the identified dental appliance engagement surface; and generating a dental appliance that accommodates the existing attachment based on the secondary treatment plan.

Any of these methods may include confirming that a total number of the attachments for the secondary treatment plan is less than or equal to a user's preference for a preferred total number of attachments. Determining that the existing attachment is suitable for activation may include determining that the existing attachment has one or more potential planes of activation that are suitable for implementing the secondary treatment plan. For example, determining that the existing attachment has one or more potential planes of activation may include determining that the existing attachment includes a surface having at least a minimum area.

In some examples generating the dental appliance comprises generating one or more digital models of the dental appliance. The current scan and the one or more prior scans may include one or more of: an intraoral scan, a cone beam computed tomography (CBCT) scan, and an x-ray. In some cases determining that the existing attachment is suitable for activation further comprises: identifying a type of the existing attachment as a molded attachment, a preformed attachment or uncertain; and determining whether the identified type of the existing attachment is usable as an active attachment. For example, identifying the type of the existing attachment may include using a trained machine learning agent.

In some examples determining that the existing attachment is suitable for activation further comprises determining that the engagement surface is suitably positioned and oriented with respect to the tooth according to an intended movement of the tooth to be implemented in the secondary treatment plan. In some cases determining that the existing attachment is suitable for activation to achieve one or more tooth movements includes determining whether the one or more existing attachments is pitted, cracked, has poor surface quality, has poor bond quality, and/or is not appropriately oriented for an intended movement of a corresponding tooth.

Any of these methods may include removing the existing attachment from the secondary treatment plan if the existing attachment is not suitable for activation to achieve one or more intended movement of the tooth to be implemented in the secondary treatment plan. The dental appliance may include an aligner and/or a palatal expander. Any of these methods may include the use of a series of dental appliances that are shaped to move the subject's teeth incrementally according to the secondary treatment plan. The existing attachment may include a dental attachment bonded to the subject's teeth and used in prior treatment plan.

The existing attachment may be a pre-formed attachment that is categorized according to a library of dental attachments. In some cases the existing attachment is a natural feature on the subject's tooth, wherein the natural feature includes a protrusion or a ridge on the subject's tooth. Any of these methods may include receiving approval, from a user, for generating the dental appliance. Any of these methods may include confirming that a user would like to use the existing attachment in the secondary treatment plan. In some cases these methods may include repeating the steps of determining the shape, determining that the existing attachment is suitable, and activating the dental appliance engagement surface for multiple existing attachments on the subject's dentition.

Also described herein are systems for performing any of these methods. For example, described herein are systems for secondary orthodontic treatment planning, the system comprising: one or more processors; and one or more memory stores coupled to one or more processors, the one or more memory stores configured to store computer instructions that, when executed by the one or more processors, perform a computer-implemented method comprising: receiving a scan of a subject's dentition including an existing attachment on the subject's dentition; determining a shape of the existing attachment based on comparing the scan to one or more prior scans of the subject's dentition; determining that the existing attachment is suitable for activation to achieve one or more tooth movements, at least partially based on the shape of the existing attachment; identify a dental appliance engagement surface of the existing attachment when the attachment is suitable for activation; generating the secondary treatment plan including applying a force to the subject's dentition via the identified dental appliance engagement surface; and generating a dental appliance that accommodates the existing attachment based on the secondary treatment plan.

In any of these systems, the scan may be received remotely from a doctor's computer system, wherein the computer-implemented method further comprises: sending a message to the doctor's computer system that the existing attachment is suitable for activation in the secondary treatment plan; and receiving a confirmation from the doctor's computer system to activate the existing attachment in the secondary treatment plan. The computer-implemented method may further comprise generating the secondary treatment plan using the activated existing attachment. The computer-implemented method may further comprise repeating determining the shape, determining that the existing attachment is suitable, and activating the dental appliance engagement surface for multiple existing attachments on the subject's dentition. In any of these systems, determining that the existing attachment is suitable for activation may further comprise: identifying a type of the existing attachment as a molded attachment, a preformed attachment or uncertain; and determining whether the identified type of the existing attachment is usable as an active attachment in the secondary treatment plan. Identifying the type of the existing attachment may include using a trained machine learning agent.

Also described herein are methods for secondary orthodontic treatment planning, the method comprising: receiving, from a user, a request to use an existing attachment on a subject's dentition in a secondary treatment plan; sending, to a treatment planning system, a current scan of the subject's dentition including the existing attachment on the subject's dentition; receiving, from the treatment planning system, an indication that the existing attachment is determined to be suitable for activation, wherein the determination is at least partially based on one or more quality assessment criteria based on a shape of the existing attachment; sending, to the treatment planning system, a confirmation accepting use of the existing attachment as an active attachment in the secondary treatment plan; and receiving a dental appliance including an attachment engagement surface that is offset with respect to a dental appliance engagement surface of the existing attachment so that the dental appliance can apply the force on the subject's dentition. The method may further include sending, to the treatment planning system, a digital three-dimensional (3D) model of a final target configuration of the subject's dentition according to the secondary treatment. For example, the method may further comprise sending, to the treatment planning system, a prior scan of the subject's dentition taken prior to placement of the existing attachment. Any of these methods may include receiving, from the treatment planning system, the secondary treatment plan using the existing attachment as an active attachment. The secondary treatment plan may include digital 3D models of the subject's dentition at multiple stages of the secondary treatment plan. The current scan may include one or more of: an intraoral scan, a cone beam computed tomography (CBCT) scan, and an x-ray.

The request to use an existing attachment may include request to use multiple existing attachments on the subject's dentition in the secondary treatment plan, the method further comprising receiving, from the treatment planning system, an indication that one or more of the multiple existing attachments are determined to be suitable for activation.

Also described herein are systems for secondary orthodontic treatment planning, the system comprising: one or more processors; and one or more memory stores coupled to one or more processors, the one or more memory stores configured to store computer instructions that, when executed by the one or more processors, perform a computer-implemented method comprising: receiving, from a user, a request to use an existing attachment on a subject's dentition in a secondary treatment plan; sending, to a treatment planning system, a current scan of the subject's dentition including the existing attachment on the subject's dentition; receiving, from the treatment planning system, an indication that the existing attachment is determined to be suitable for activation, wherein the determination is at least partially based on one or more quality assessment criteria based on a shape of the existing attachment; sending, to the treatment planning system, a confirmation accepting use of the existing attachment as an active attachment in the secondary treatment plan; and receiving a dental appliance including an attachment engagement surface that is offset with respect to a dental appliance engagement surface of the existing attachment so that the dental appliance can apply the force on the subject's dentition.

Any of these systems may include sending, to the treatment planning system, a digital three-dimensional (3D) model of a final target configuration of the subject's dentition according to the secondary treatment plan. In some cases the system and/or method may be configured to include sending, to the treatment planning system, a prior scan of the subject's dentition taken prior to placement of the existing attachment.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings.

DETAILED DESCRIPTION

Figure 1A:
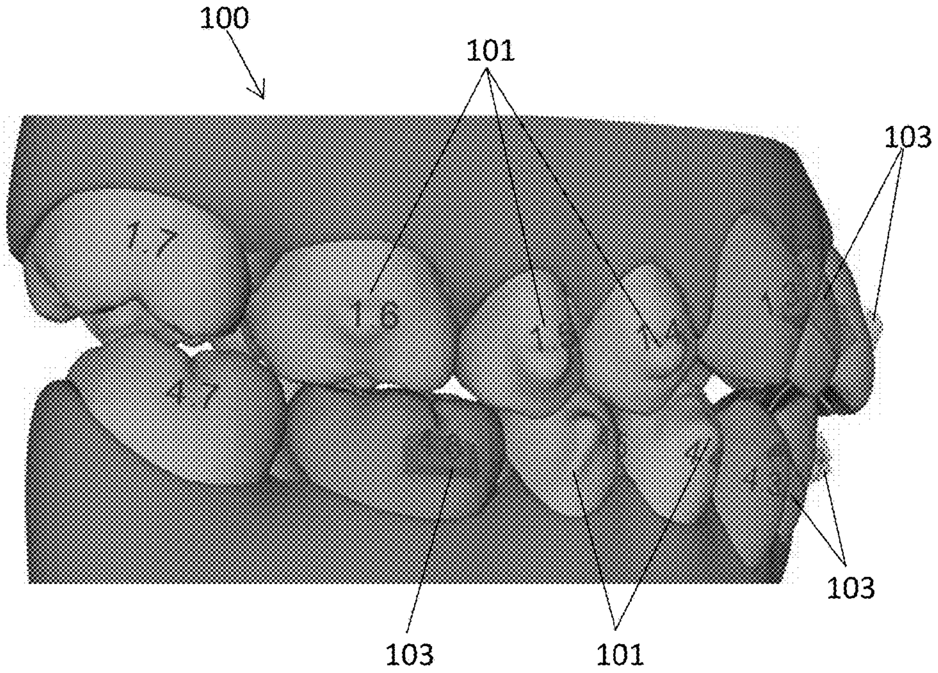
FIG. 1A illustrates an example of a digital dentition model created from a scan of a subject's dentition.

Described herein are apparatuses (e.g., systems and devices, including software) and methods of orthodontic treatment planning for analyzing attachments that are already on a patient's teeth and determining whether the attachments may be activated as part of subsequent treatment plan. The existing attachment may have been used to apply repositioning forces on a tooth in a prior dental treatment (or prior portion of dental treatment) but may not be configured to actively engage with a current or subsequent dental appliance in a manner that applies a repositioning force on the tooth. The methods and apparatuses described herein provide a way for dental professionals to determine whether any existing attachments on a patient's teeth can be 'activated' for use in a current or subsequent dental plan. If the practitioner decides to activate one or more of the existing attachments, a treatment plan may be created based on activating the one or more existing attachments.

Traditionally, an existing attachment is either removed from the patient's tooth or is allowed to remain on the patient's tooth but not actively engage with a dental appliance in a manner that applies a repositioning force on the tooth. For example, a passive attachment may be configured to simply act as an anchor to help retain the dental appliance on the patient's dentition.

The methods and systems described herein provide a way for the dental practitioner to minimize such dental attachment removal procedures. In addition, the methods and systems may provide an opportunity for the dental practitioner to adjust the treatment plan, during the course of treatment, in a manner that uses one or more of the passive attachments.

The repositioning forces applied to the teeth by a dental appliance through an active attachment may be in accordance with an orthodontic treatment plan. The orthodontic treatment plan may include a series of stages in which the subject's teeth are incrementally moved from the initial configuration toward a target configuration. For example, the teeth may be straighter in the target configuration compared to the initial configuration. Each of the treatment stages may be implemented by applying forces on one or more of the subject's teeth according to that treatment stage. The forces may be directed in a predetermined direction and with a predetermined amount of force to move the teeth toward a target configuration for that particular stage. Each of the stages of the treatment plan may be associated with a corresponding dental appliance (e.g., aligner, palatal expander, etc.).

The dental appliances may include any type of dental appliance that is configured to cooperate with attachments on the teeth to apply forces on the teeth. In some cases, the dental appliances include shell aligners that are made of one or more polymer materials and that are configured to resiliently apply the forces to the teeth. In some examples, the aligners are clear aligners that are made of a transparent or translucent polymer material. In some cases, the dental appliances include palatal expanders that are configured to apply an expansion force for expanding the subject's palate. In some examples, the palatal expanders may be configured to apply an expansion force for expanding the subject's palate and tooth repositioning forces repositioning one or more teeth (e.g., to straighten teeth).

FIG. 1A shows an example of a digital dentition model 100 created based on a scan of a subject's dentition. The scan was taken after at least a portion of treatment plan (e.g., previous or primary treatment plan) was implemented. The dental practitioner may have determined that further adjustments to the teeth are necessary and would like to implement a secondary treatment plan. For example, the dental practitioner and/or patient may want to make minor adjustments (a.k.a., refinements) to the tooth positions. Refinements may be used to straighten or un-crowd teeth, adjust the bite, and/or close gaps between teeth. In some cases, more substantive adjustments and tooth movements are needed. Although palatal expansion is usually the primary (initial) treatment, occasionally the secondary treatment plan may include applying palatal expansion forces on the dentition instead of or in addition to applying repositioning forces on the teeth (e.g., for straightening).

The scan of the dentition is taken with existing attachments 101 the teeth. The existing attachments 101 may be made of material that was previously bonded to the teeth, and which may have been used in one or more stages of the previous treatment plan. In some cases, an existing attachment 101 may be another type of existing feature on the subject's tooth, such as a natural feature (e.g., protrusion, ridge) of the subject's tooth.

Treatment planning software may use the digital dentition model 100 to calculate a final or target configuration of the teeth according to the secondary treatment plan. For example, the treatment planning software may determine what forces to apply to the teeth of the digital dentition model 100 to achieve the final or target tooth configuration and one or more intermediate tooth configurations for intermediate stages of the secondary treatment plan. As part of secondary treatment planning, new attachments 103 may be virtually placed on the dentition model 100. The treatment planning software may be used to calculate the shapes, locations, and the orientation of the new attachments 103 relative to the teeth.

Traditionally, some or all of the existing attachments 101 are removed from the digital dentition model 100. If any of the existing attachments 101 remain on the teeth, they are typically used as passive attachments, but without activating them to specifically target the application of force to move the teeth. Passive attachments are attachments that are on the patient's teeth but are not configured to actively engage with a dental appliance to apply planned repositioning forces on the teeth.

Figure 1B:
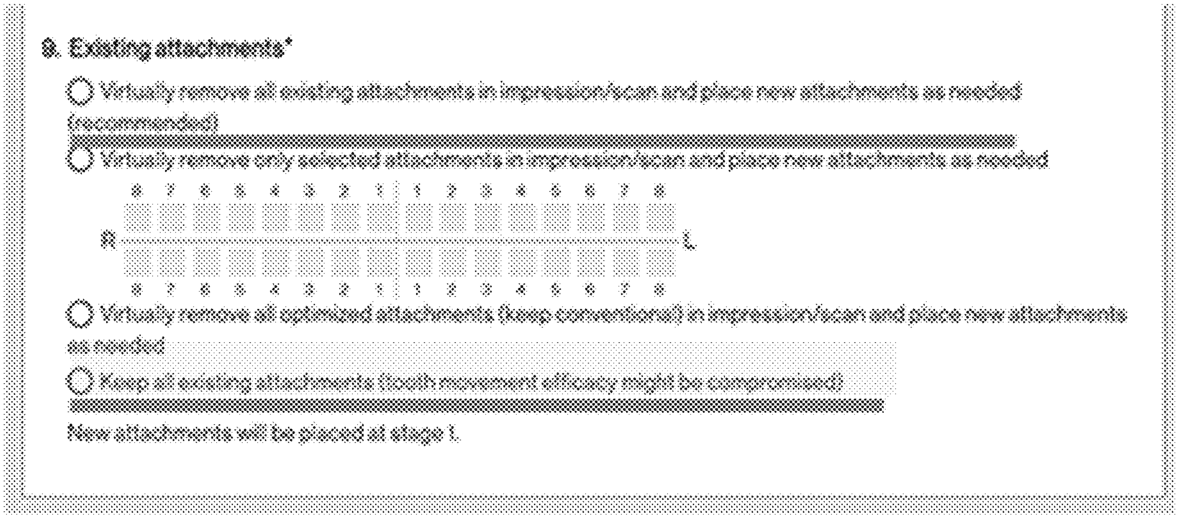
FIG. 1B illustrates an example of a user interface representing a traditional way of handling existing attachments.

FIG. 1B shows an example of a user interface representing a traditional way of handling existing attachments. As shown, the user can choose to virtually remove all the existing attachments, virtually remove only selected existing attachments, virtually remove all optimized attachments, or keep all existing attachments. If the dental practitioner chooses to virtually remove all of the existing attachments 101, the treatment planning software will calculate the secondary treatment plan with only the new attachments 103. If the dental practitioner chooses to virtually remove some of the existing attachments 101, the treatment planning software will calculate the secondary treatment plan with the new attachments 103 implementing the repositioning forces and with the remaining existing attachments implemented as anchoring attachments, which do not implement repositioning forces on the teeth. The dental practitioner will need to physically remove any of the existing attachments from the patient's teeth that were virtually removed from the virtual model 100 in order to implement the secondary treatment plan. Leaving the existing attachments as passive attachments may compromise the efficacy of tooth movement. Therefore, it is typically recommended to remove all existing attachments. However, removing existing attachments is time consuming for the dental practitioner and the patient. Furthermore, the dental practitioner may be removing perfectly good attachments that are good enough to use in the secondary treatment plan. Thus, attachment removal may be wasteful and an inefficient way of treatment planning.

Figure 2A:
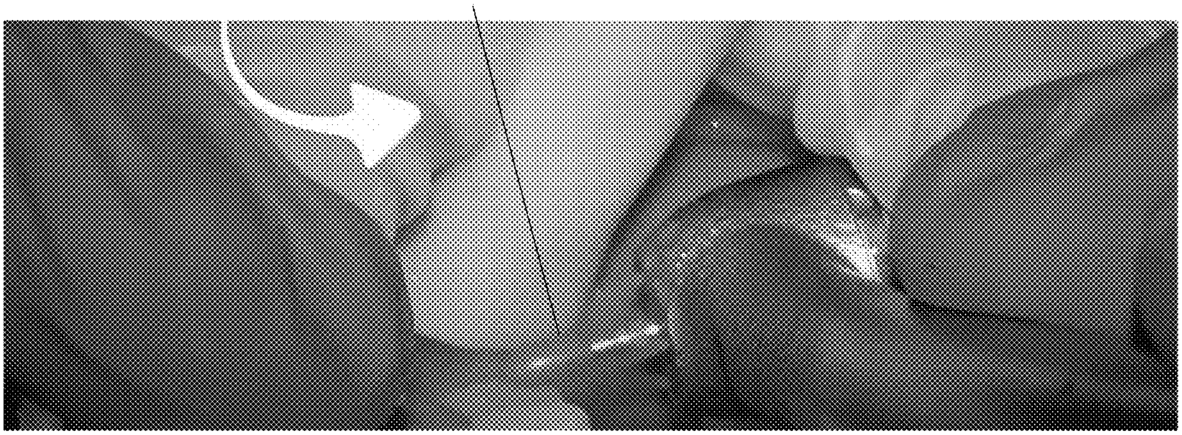
FIGS. 2A-2C illustrate examples of physical removal of attachments from a subject's teeth.
Figure 2B:
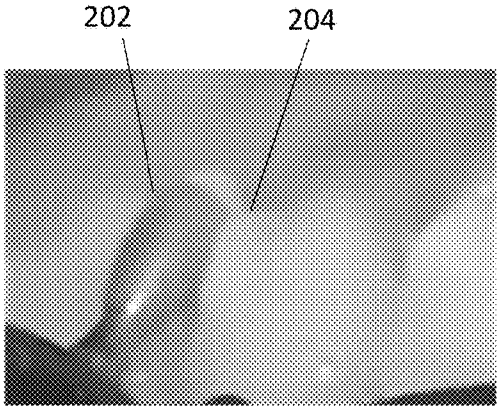
Figure 2C:
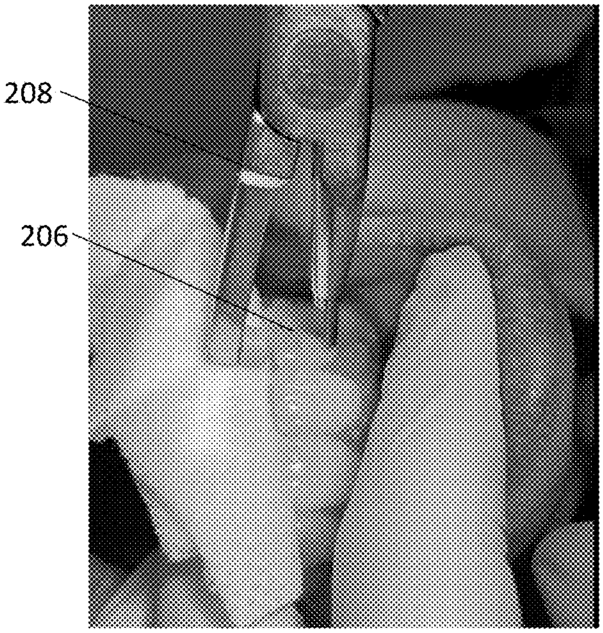

FIGS. 2A-2C show examples of physical removal of attachments from a patients' teeth. FIGS. 2A and 2B show a high-speed burr 202 being used to grind off a 'molded' dental attachment 204. Such practice may create dust, debris and produce unpleasant sounds. FIG. 2C shows removal of a 'preformed' dental attachment 206—in this case, using pliers 208 to pry off the attachment 206.

Figure 3A:
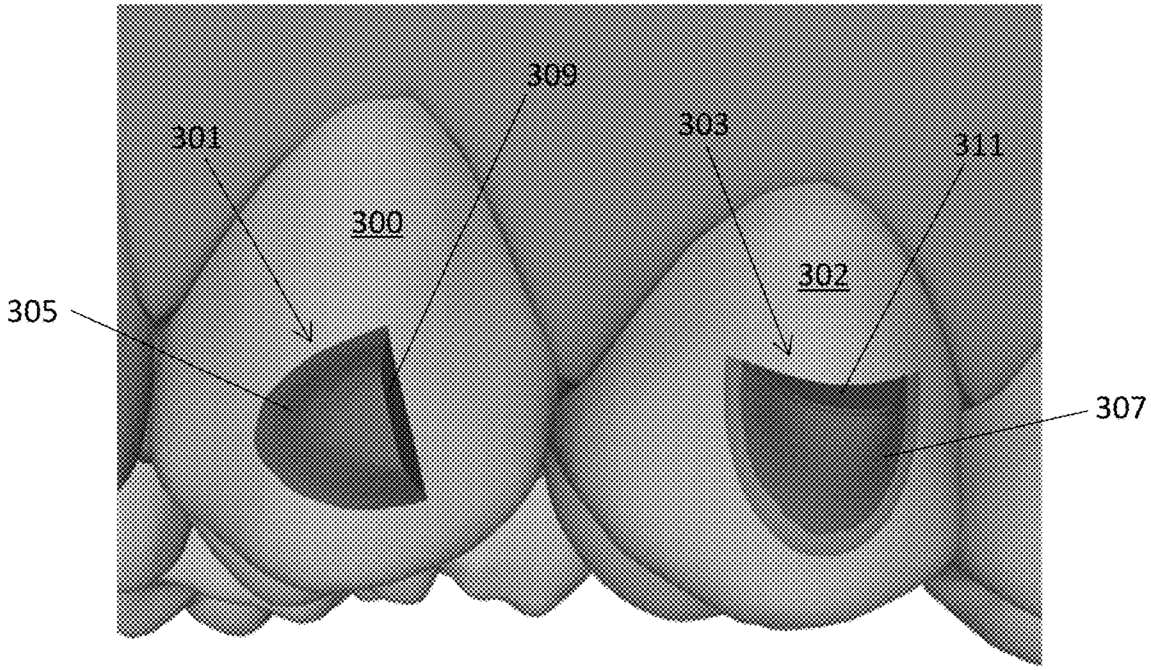
FIGS. 3A-3C illustrate differences between passive and active attachments.
Figure 3B:
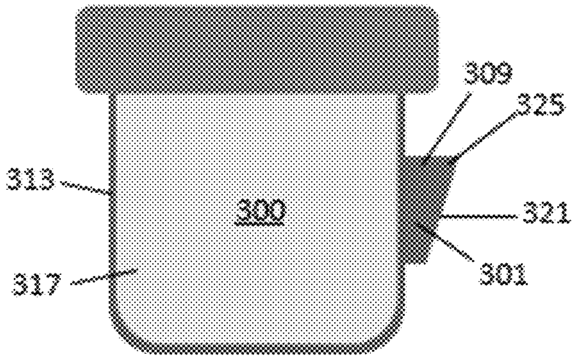
Figure 3C:
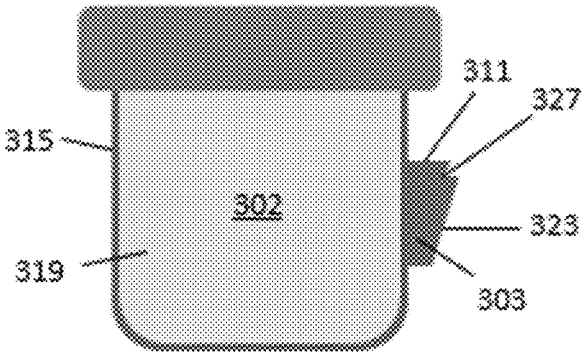

FIGS. 3A-3C illustrate differences between passive and active attachments. FIG. 3A shows a passive attachment 301 (also referred to as a 'white' attachment) on a first tooth 300 and an active attachment 303 (also referred to as a 'red' attachment) on a second tooth 302 of a dentition. In this case, each of the passive and active attachments 301/303 have a roughly hemispherical shape with a curved outer surface 305/307 and a flat appliance engagement surface 309/311. According to the secondary treatment plan, the appliance engagement surface 311 of the active attachment 303 is configured to engage with a corresponding dental appliance such that the dental appliance applies a tooth repositioning force on the second tooth 302 in a predetermined direction (e.g., toward the engagement surface 311) with a predetermined force magnitude. However, the appliance engagement surface 309 of the passive attachment 301 is not configured to apply a tooth repositioning force on the first tooth 300 in the secondary treatment plan. For example, the dental appliance may engage with the passive attachment 301 to anchor the dental appliance to the dentition but not apply any tooth repositioning force according to the secondary treatment plan.

FIGS. 3B and 3C further illustrate differences between passive and active attachments. FIG. 3C shows a shape difference between a dental appliance 315 (e.g., aligner) and the second tooth 302. The dental appliance 315 defines a second cavity 319 that is shaped to fit over the second tooth 302. The second cavity 319 includes a second attachment cavity 323 defined by walls that are configured to engage with the appliance engagement surface 311 of the active attachment 303. For example, the second attachment cavity 323 has an attachment engagement surface 327 that is offset with respect to the appliance engagement surface 311 when the dental appliance 315 is placed on the second tooth 302. This offset creates a force that is transferred from the dental appliance 315 through the active attachment 303 to the second tooth 302 in a predetermined direction (e.g., toward the engagement surface 311) and with a predetermined force magnitude according to the treatment plan.

FIG. 3B illustrates a shape difference between the dental appliance 315 and the first tooth 300. The dental appliance 315 defines a first cavity 317 that is shaped to fit over the first tooth 300, and that includes a first attachment cavity 321 defined by walls that are shaped according to the dimensions of the passive attachment 301. Unlike in the case of the active attachment 303 of FIG. 3C, the first attachment cavity 321 does not include a wall that is offset with respect to the appliance engagement surface 309 of the passive attachment 301. Thus, there is no repositioning force applied to the tooth 300 when the dental appliance 315 is placed on the first tooth 300. However, the passive attachment 301 may act as an anchor for anchoring the dental appliance 315 on the dentition, for example, by helping to maintain the dental appliance 315 on the dentition. Although such anchoring may be useful, the passive attachment 301 may not allow another active attachment to be placed on the first tooth 300. The methods and apparatuses described herein may be used to create a secondary treatment plan that can actively use of the passive attachment 301, thereby 'activating' the passive attachment 301.

Figure 4A:
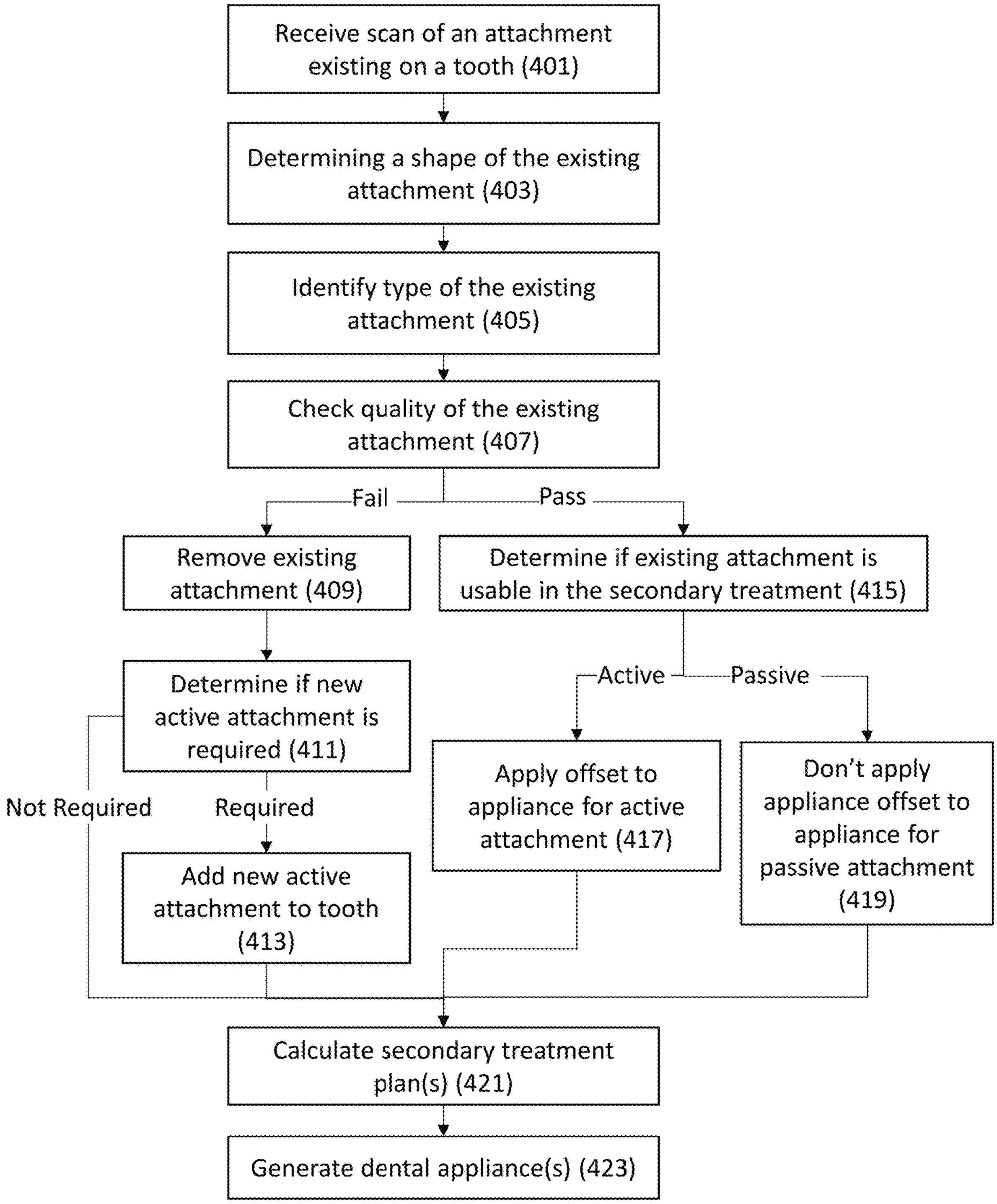
FIG. 4A is an example flowchart illustrating an example process for determining whether to activate an existing attachment and for activating an existing attachment.

FIG. 4A is a flowchart showing an example process for determining whether to activate and how to activate one or more existing attachments as part of a secondary treatment plan. A scan of an existing attachment on the tooth is received (401). The scan may include one or more images of a dentition of a patient, including the existing attachment on the tooth. In some examples, the scan is a three-dimensional (3D) scan. The scan may be any of a number of types of scans. For example, the scan may be an intraoral scan. The scan may be taking using any of number of scanning techniques and technologies, such as using visible light scanning, ultraviolet light scanning, infrared scanning, and/or x-ray scanning (e.g., cone beam computed tomography (CBCT)).

The scan is used to determine a shape of the existing attachment (403). This identification may be done automatically (e.g., once the dental practitioner requests the analysis). In some examples, identifying the shape of the existing attachment involves comparing the scan (current scan) of the existing attachment on the tooth to a prior scan of the existing attachment on the tooth. Such prior scan may be, for example, from implementation of a prior treatment plan using the existing attachment. The current scan may be segmented to distinguish between the existing attachment and the tooth, and a current 3D model of the dentition may be generated based on the current scan. In some examples, the existing attachment may be labeled in the current 3D model. The current 3D model may be compared to a prior 3D model of the dentition generated based on the prior scan of the dentition prior to placement of the existing attachment. Based on prior treatment plan, we should know what kinds of attachments were previously placed. The shape of the existing attachment can be derived by 'subtracting' the tooth shape of the prior 3D model from the tooth shape of the current 3D model. Thus, this difference calculation can be used to determine the shape of the existing attachment.

In some examples, the type of the existing attachment may optionally be identified (405). The type of existing attachment may relate to its function, material and/or the way in which the attachment was formed. For example, the existing attachment may be identified as being a 'preformed' attachment, a 'molded' attachment, or other (e.g., uncertain). Molded attachments are shaped using a mold (sometimes referred to as a 'template') that is placed on the patient's teeth. For example, the template may include an attachment cavity that is shaped as a negative impression of the attachment. An attachment material, while in malleable form, is placed into the attachment cavity such that the attachment material takes on the desired attachment shape. The template is then placed onto the patient's dentition to position the attachment cavity with the attachment material to a particular attachment location on the patient's tooth. The attachment material is then cured (e.g., via light or heat) and bonded to the patient's tooth. When the template is removed from the patient's dentition, the hardened attachment remains bonded to the patient's tooth.

Preformed attachments are different from molded attachments in that they are formed prior to placement on the patient's teeth. The preformed attachments may be chosen from a library of attachments having different shapes, flexibility characteristics, and/or material characteristics. The library may of the different preformed attachments, with associated characteristics, may be saved in a database. Preformed attachments may be removably attached to a tray that fits on the patient's teeth to position and orient the attachments at particular attachment locations on the teeth.

Identifying the type of attachment may be important when preformed and molded attachments have different material characteristics and/or wear characteristics (e.g., during the time that the attachment is in the patient's mouth). For example, certain kinds of dental appliances may be able to leverage reactivation of preformed attachments but not molded attachments, or vice versa. Different kinds of dental appliances may include thermoformed aligners, directly fabricated aligners, thermoform retainers that use attachments, directly fabricated retainers that use attachments, and palatal expanders. In some cases, a dental appliance may be able to actively use either preformed or molded attachments.

In some examples, a machine learning agent is used to identify or assist in the identification of the type of attachment. Any type of machine learning agent and associated analysis techniques may be used, such as one or more of: neural networks, decision trees, support-vector machines, regression analysis, Bayesian networks, Gaussian processes, and/or genetic algorithms. The training data set for teaching the machine learning agent may include digital 3D models based on prior scanned images of attachments. In some cases, the training data set includes a library of attachments (e.g., preformed attachments) that have already been identified and characterized (e.g., labeled) based on their shapes, function and/or other characteristics. In some examples, the existing attachment in the scan may be identified based on color analysis (e.g., using RGB data). For example, color (RGB) data and shape data from the scan may be used to identify specialized attachments (e.g., a button attachment). See, e.g., FIG. 7D.

Once the attachment shape is identified, the quality of the existing attachment is checked (407) to determine whether the attachment has sufficient quality/fidelity for active use in the secondary treatment plan. This determination may be based on one or more quality assessment criteria. In some cases, this involves identifying any potential active surfaces of the existing attachment for supporting an applied force by the dental appliance according to the secondary treatment plan. For example, a potential active surface may have at least a minimum surface area. The evaluation may involve determining whether the shape of the attachment is sufficiently preserved (after being in the patient's mouth) to activate.

In some cases, the shape of the existing attachment is compared to an 'ideal' shape of the same attachment type. Such an ideal shape may be based on one or more attachment shapes saved in computer memory (e.g., database) categorized by type. The existing attachment may be given a 'score' of how close its shape compares to the 'ideal' attachment shape. For example, an existing attachment may be given a high score if its shape is close to the ideal shape or a low score if its shape is not close to the ideal shape. In some cases, a low score may mean it has not been adequately identified. The existing attachment may 'pass' the quality check if the score is at or above a threshold value, and 'fail' the quality check if score is below the threshold value.

If the existing attachment fails the quality check, the system removes the existing attachment from the calculation of the secondary treatment plan (409). The system may provide a message for the user (e.g., dental practitioner) recommending removal of the attachment from the patient's tooth.

A determination may optionally be made to determine whether a new active attachment is required (or should be used) to implement the secondary treatment plan (411). For example, the tooth and/or an attachment may be identified as critical to the remaining tooth movement. In this case, the new active attachment may be selected to replace the removed existing attachment. One or more treatment plans is/are then calculated (421) using the new active attachment, and one or more dental appliances are generated (423) based on a selected treatment plan. If a new active attachment is not required, one or more treatment plans can then be calculated (419) with the existing attachment removed (without a new active attachment). One or more dental appliance(s) may then be generated (421) based on a selected treatment plan.

Generating the dental appliance(s) may involve generating the dental appliance(s) in virtual space (e.g., as one or more virtual dental appliances). Additionally or alternatively, generating the dental appliance(s) may involve generating the dental appliance(s) as physical appliance(s), e.g., using one or more manufacturing processes (e.g., thermoforming, 3D printing, extrusion, etc.).

Returning to (407), if the existing attachment passes the quality check, a determination is made as to whether the existing attachment is to be usable in the secondary treatment (415). This can involve determining whether the existing attachment has a sufficient potential plane of activation for applying the repositioning force from the dental appliance. The one or more potential planes of activation may be digitally identified. For example, a potential plane of activation may be sufficiently flat to support the force applied to it from the dental appliance. In addition, the potential plane of activation should be sufficiently positioned and oriented on the tooth for activation according to the secondary treatment plan. The type of the existing attachment (e.g., preformed, molded, or other) identified at (405) can also factor into the determination as to whether the existing attachment is useable for the secondary treatment.

If the existing attachment is determined to be useable for activation, the surface having a sufficient plane of activation may be activated as a dental appliance engagement surface—a surface that the dental appliance will engage with and apply a repositioning force onto the tooth. When creating a digital model of the dental appliance, an offset is applied to the dental appliance (417). The offset corresponds to a dimensional offset of an attachment engagement surface of the dental appliance that allows the dental appliance to apply the repositioning force against the dental appliance engagement surface of the attachment. Once the offset is applied to the dental appliance, one or more treatment plans are calculated (419) and one or more dental appliances may be generated (423).

If the existing attachment is determined to not to be usable for activation, it may be used as a passive attachment. For example, the existing attachment may not have a potential active surface that is properly positioned and/or oriented for activation according to the secondary treatment plan. For a passive attachment, no offset is applied to the dental appliance (419). For example, an attachment cavity of the dental appliance may be shaped to cover the attachment and be used an anchor but not configured to apply a repositioning force on the tooth. One or more treatment plans may then be calculated (421) and one or more dental appliances may be generated (423).

The existing attachment can be identified/marked (e.g., auto-segmenting) as either a passive or active attachment based on the analysis at (415). Alternatively, the existing attachment may be determined to not be usable as either an active attachment or a passive attachment; in which case, the existing attachment may be removed from the secondary treatment plan.

Calculating one or more secondary treatment plans (421) may include calculating forces on the tooth to move the tooth toward a final/desired position of the secondary treatment. A series of 3D models for the current tooth position, intermediate position(s) and final/desired position can be calculated. Generating one or more dental appliances (423) can include generating a series of dental appliances that are configured to incrementally move the teeth (e.g., a digital model of the dentition or of the physical dentition) according to the secondary treatment plan(s).

If nearly all the existing attachments in the scan do not qualify for activation, an optional step may include considering an alternative manufacturing to develop a treatment plan that achieves the desired tooth movement. Alternative manufacturing may include direct fabrication of the dental appliance(s) by tuning the dental appliance(s) to compensate for the poor input attachment shapes.

Some or all the steps 401-423 may be performed iteratively for each existing attachment on a patient's dentition. In some cases, the analysis is performed until the dental practitioner's preference is met. For example, a goal may be to maximize the use of existing attachments. Maximizing the use of existing attachments can save the dental practitioner and the patient time and money by minimizing the number of attachments that need to be removed and/or rebonded.

Figure 4B:
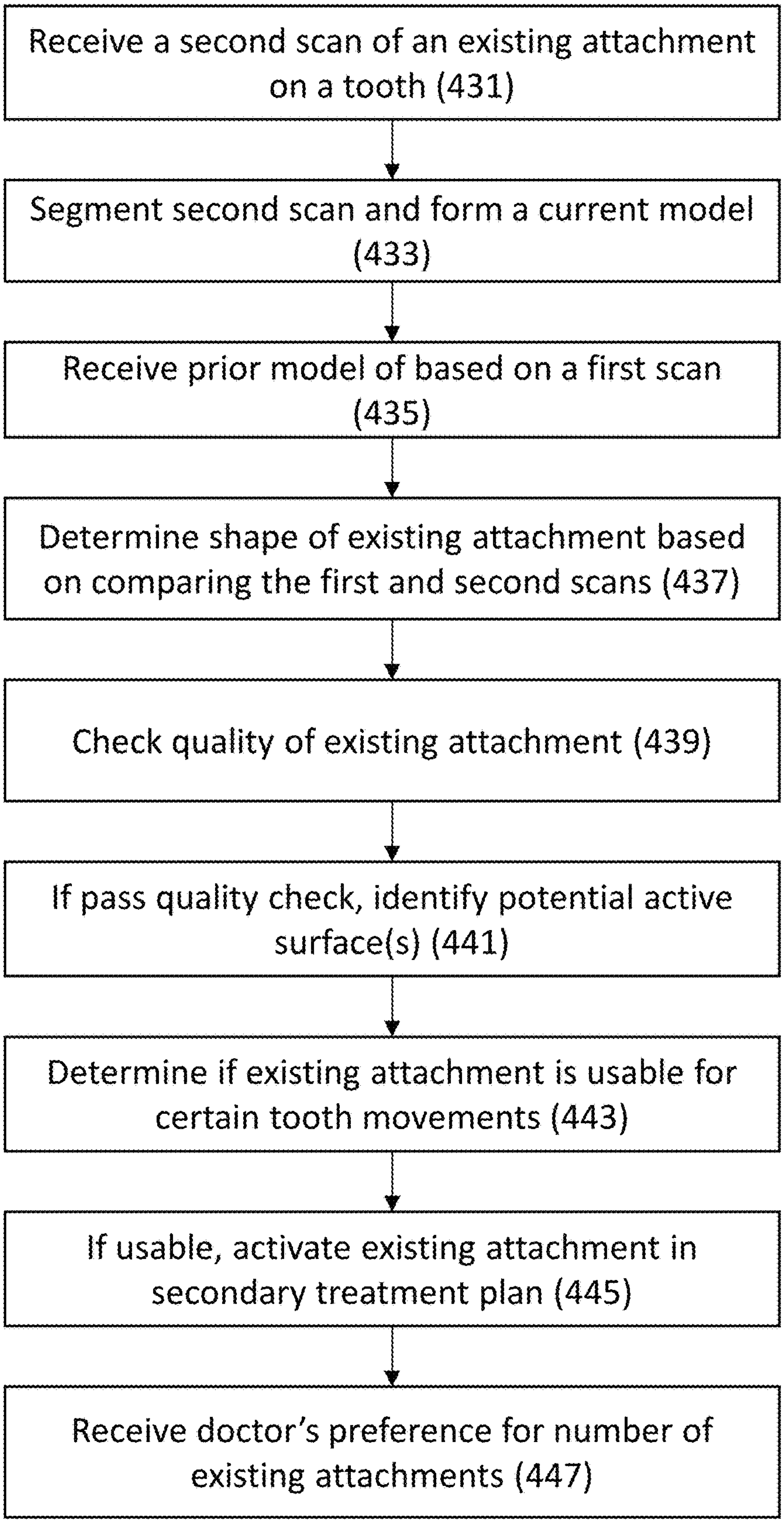
FIG. 4B is another example flowchart illustrating an example process for determining whether to activate an existing attachment and for activating an existing attachment.

FIG. 4B is another example flowchart showing an example process for determining whether and how to activate existing attachments for a secondary treatment plan. A second scan of the patient's teeth with an existing attachment is received (431). As discussed, the second scan may be taken because the dental practitioner is considering implementing, or has decided to implement, a secondary treatment plan to further reposition a patient's teeth.

The second scan is segmented, and a current digital 3D model of the dentition is formed (433). A prior digital 3D model based on a first scan of the of the dentition is received (435). The first scan may be of the patient's dentition prior to placement of the existing attachment. The shape of the existing attachment is determined based on comparing the first and second scans (437). For example, the prior 3D model may be subtracted from the current 3D model to subtract out the tooth and leave the existing attachment.

The quality of the existing attachment is checked (439). The quality check may include determining whether the shape of the existing attachment is sufficiently well defined and preserved for activation. As discussed, this may involve comparing the shape of the existing attachment to an 'ideal' shape (of the same type of attachment). For example, if the attachment shape is already known from the prior treatment, this shape may be used as the ideal shape. The shape of the existing attachment may be evaluated to determine whether it has sufficient surfaces, volume, and integrity, as described herein.

If the existing attachment passes the quality check, one or more potential active surfaces may be identified (441). For example, one or more surfaces of the existing attachment may be identified and evaluated to determine whether the surface(s) may act as potential planes of activation. Once potential active surface(s) are identified, a determination is made as to whether the existing attachment is useable for certain tooth movement according to the secondary treatment plan (443). This may depend, for example, on the position and orientation of the potential planes of activation of the existing attachment with respect to expected repositioning forces applied to the tooth.

If the existing attachment is determined to be useable, the existing attachment is activated for use in the secondary treatment plan (445). For example, a calculation of new solutions for tooth movement based on a final position of the secondary treatment plan can be triggered. Once all existing attachments are analyzed for whether they can be activated, this information can be sent to the doctor, and the doctor can send his/her preference for the number of existing attachments to activate (447).

Figure 4C:
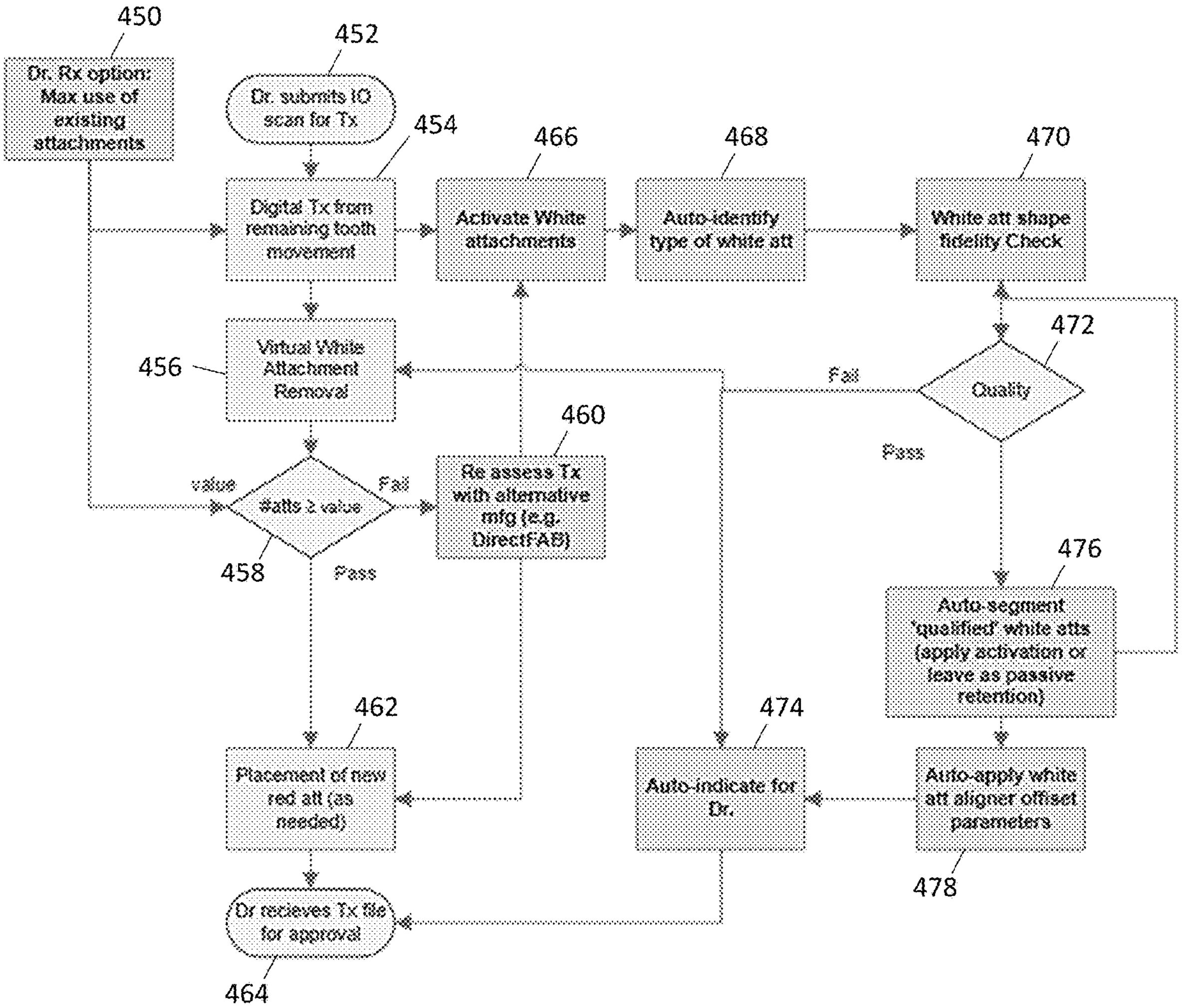
FIG. 4C is a further example flowchart illustrating an example process for determining whether to activate an existing attachment and for activating an existing attachment.

FIG. 4C is another example flowchart showing an example process for determining whether and how to activate existing attachments for a secondary treatment plan. A doctor makes a request to maximize the use of existing attachments on a patient's dentition (450). For example, the doctor may want to minimize removal of one or more existing attachments from the patient's teeth. In addition, the doctor submits a scan (e.g., from an intraoral (IO) scan) of the patient's dentition for treatment (Tx) (452). A secondary treatment plan is created for completing the remaining tooth movement necessary to achieve a target tooth configuration (454). In current processes, instead of giving the doctor the option to maximize use of existing attachments (450), the existing ('white') attachments are removed virtually from the digital model(s) as part of the treatment plan (456). If it is determined that one or more new ('red') attachments are needed, a decision is made as to whether the number of new attachments is greater than a predetermined value (458). If the number of attachments is greater than the predetermined value, the new ('red') attachments are placed virtually on the digital model(s) as part of the treatment plan (462), and the doctor is provided a treatment plan for approval (464).

If it is determined that too many existing attachments are flagged from removal (e.g., greater than the predetermined value) (458), the treatment plan is reassessed with an alternative manufacturing process (460). For example, direct fabrication may overcome attachment shape challenges. New ('red') attachment may then be virtually placed on the digital model and used to create a treatment plan (462). The treatment plan can then be provided to the doctor for approval (464).

If an analysis of whether to activate existing ('white') attachments is made (466), the type of the existing ('white') attachments are identified (468). Identifying the type of attachment may include identifying whether it is a molded attachment or preformed attachment, as described herein. Alternatively or additionally, identifying the type of attachment may include identifying whether the attachment is used for translation, rotation, intrusion, or extrusion. Alternatively or additionally, identifying the type of attachment may include identifying whether the attachment is a specialized attachment (e.g., button, power arm, bite-ramp, or for use with a specialized appliance (e.g. distalizer)). In some cases, identifying the type of attachment may include using a machine learning agent (e.g., Computer Vision-Machine Learning (CV-ML) model). Additionally or alternatively, this may include using scan color data (e.g., RGB data) and/or shape data from the scan. For example, scan color data and shape data may be used to help identify a button type of attachment, which may be difficult to identify using other techniques.

Once the type(s) of the attachment is/are identified, the shape of the attachment may be analyzed to check the fidelity of the attachment. Considerations may include whether the attachment has any de-bonded locations, whether the surface of the attachment is of sufficient integrity and/or whether the shape of the attachment is sufficient. In some examples, the attachment type is set as 'agnostic' (e.g., which may allow a rotation type of attachment to be analyzed the same as an extrusion type of attachment). Optionally, the quality assessment may include differentiating between features on the attachment that are truly on the surface of the attachment or whether they are a result of scanning technique errors/issues.

As a result of the quality analysis (472), if the attachment is not considered to be of sufficient quality ('fail'), the system informs the doctor that the existing attachment quality is not sufficient (474), and a treatment plan is provided to the doctor for approval (464). If the existing attachment is of sufficient quality ('pass'), the qualified existing attachments are segmented and flagged as either an active attachment or a passive attachment (476). If the existing attachment is flagged as an active attachment, the active engagement surfaces of the active attachment are identified and used to create an offset for the dental appliance (478). The secondary treatment plan may be created, for example, by modifying existing treatment plan rules. The doctor is notified that one or more of the existing attachments are activated (474), and a treatment plan is provided to the doctor for approval (464).

Some of the factors in determining whether an existing attachment that is already on a patient's tooth can or should be activated include the shape fidelity and durability of the existing attachment. For example, if the existing is made of a composite material (e.g., composite polymer material) that is bonded on the patient's tooth, the attachment may have undergone some wear from being in the patient's mouth, especially if the attachment was used as an active attachment in a previous stage of a treatment plan. Such wear may have degraded the engagement surface of the attachment such that the attachment is not suitable for further use. The shape and integrity of the attachment may also depend on whether the attachment has any defects that could degrade the integrity of the attachment and/or the material of the attachment.

As described previously (e.g., step 453 in FIG. 4B), a type of the existing attachment may be identified based on characteristics identifiable in the scan(s). Identifying the type of attachment may be useful in determining how to check the fidelity of the attachment (e.g., step 455 in FIG. 4B). In some examples, the type of attachment may include a molded attachment or a preformed attachment (also referred to as a prefabricated attachment).

Figure 5A:
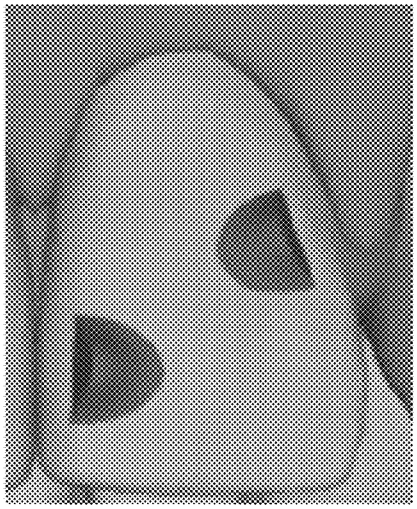
FIGS. 5A-5C illustrate examples of molded and preformed attachments.
Figure 5B:
Figure 5C:
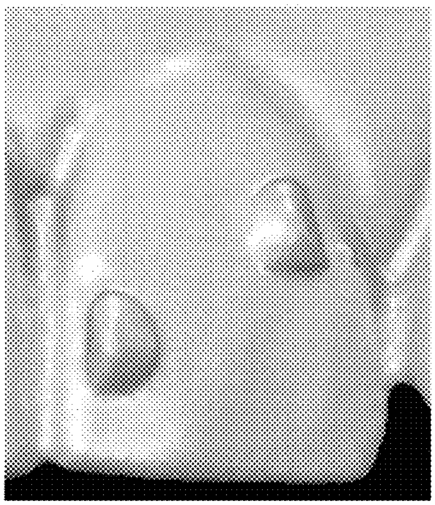

FIGS. 5A-5C illustrate examples of molded and preformed attachments. FIG. 5A shows a digital model (e.g., 3D digital model) of two attachments bonded on a tooth. The digital model may be used as a basis for forming the actual physical attachments for bonding on a patient's tooth.

FIG. 5B shows a scan of a tooth with 'molded' attachments that are formed based on the digital attachments of FIG. 5A. The molded attachments are formed using a 'template' that is an aligner-like tray having attachment cavities with negative shapes corresponding to the shapes of the attachments in the digital model of FIG. 5A. A composite material, while in a malleable state, is placed into the attachment cavities of the attachment template, then the attachment template is placed on the tooth. The composite material is then hardened (e.g., cured by exposure to ultraviolet light radiation) and the attachments are bonded to the tooth. The scan in FIG. 5B shows the shapes of the attachments formed using this technique.

FIG. 5C shows a scan of a tooth with preformed attachments using a different technique. This technique involves bonding the preformed attachments, which have already been formed according to the shapes of the digital attachment models of FIG. 5A prior to bonding on the tooth. In some cases, the preformed attachments may have shapes according to a library of dental attachments having different shapes to accomplish different tooth movements (e.g., translation, rotation, intrusion, and/or extrusion). If so, the scan of the preformed attachments may be compared the library to identify the expected shapes of the preformed attachments. In some cases, an attachment placement device that fits on the teeth is used to place the attachments at predetermined locations and at predetermined orientations with respect to the tooth. In some examples, the preformed attachments are formed using a three-dimensional (3D) printing technique. In some examples, the preformed attachments are made of a different type of material than the molded attachments (FIG. 5B) and may have different wear characteristics than the molded attachments. The preformed attachments may be bonded to the tooth using an adhesive. In some cases, the adhesive includes a curable material (e.g., curable by exposure to ultraviolet light radiation).

In some cases, the type of existing attachment is known. For example, the dental practitioner may have a record of whether the attachment was a molded or preformed attachment. Alternatively or additionally, the type of existing attachment is determined by analysis of the scan. For example, preformed attachments may have distinctive shapes and/or wear characteristics that differ from molded attachments.

The shape fidelity/quality of an attachment may be determined using one or more scans (e.g., FIGS. 5B, 5C) of a patient's teeth with the attachments already on the teeth. The determination may be accomplished using any of a number of computer analysis and/or shape recognition techniques. In some cases, such a determination may be made automatically, for example, based on the determined attachment type. In some examples, one or more machine learning techniques are used to make the determination.

Figure 6A:
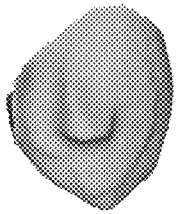
FIGS. 6A and 6B illustrate examples of dental scans showing examples of existing attachments that may be determined to have acceptable quality for activation.
Figure 6B:
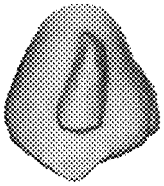

FIGS. 6A and 6B are dental scans showing examples of existing attachments that may be determined to have acceptable quality for activation. These attachments may 'pass' an attachment quality check based on shape attributes. FIG. 6A shows a scan of an existing attachment that is a molded attachment, such as described above with respect to FIG. 5B. FIG. 6B shows a scan of an existing attachment that is a preformed attachment, such as described above with respect to FIG. 5C.

In FIGS. 6A and 6B, each of the attachments may be sufficiently intact and have a sufficiently prominent engagement surface for engaging with and transmitting a tooth repositioning force from a corresponding dental appliance. Such determination may be based on whether the shape of the existing attachment has a flat enough and prominent enough surface to act as an engagement surface, has a sufficient volume or mass, is missing one or more attachments, has any voids (e.g., air bubbles), is a result of a scan error (e.g., has pitting, holes, and/or stitching errors), and/or there is underlying tooth surface having flash. In the case of preformed attachment of FIG. 6B, this determination may be based at least in part on a comparison of the scanned image of the attachment with an identified attachment shape of a library of attachment shapes.

Figure 7A:
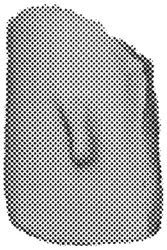
FIGS. 7A-7L illustrate examples of dental scans showing examples of existing attachments that may be determined not to have acceptable quality for activation.
Figure 7B:
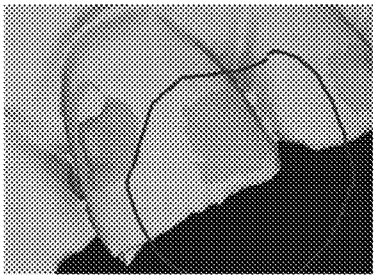
Figure 7C:
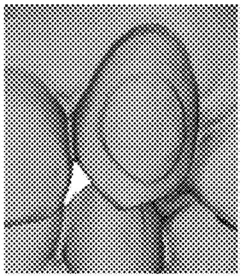
Figure 7D:
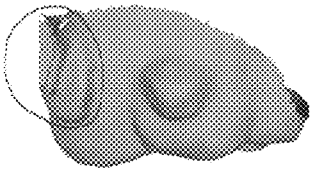
Figure 7E:
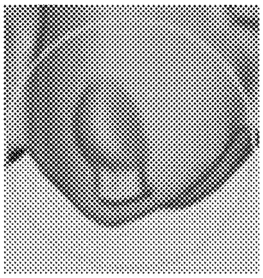
Figure 7F:
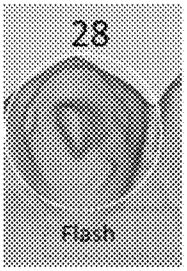
Figure 7G:
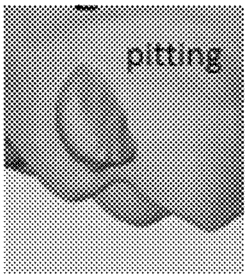
Figure 7H:
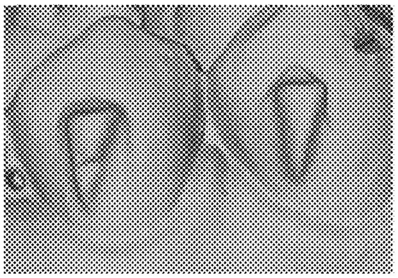
Figure 7I:
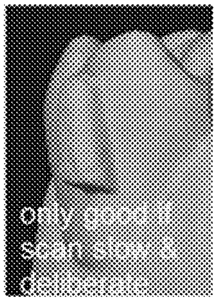
Figure 7J:
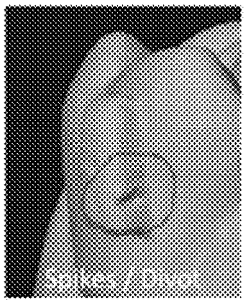
Figure 7K:
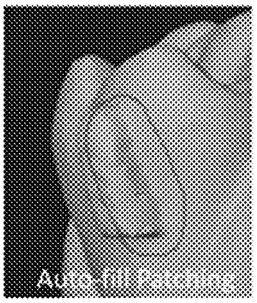
Figure 7L:
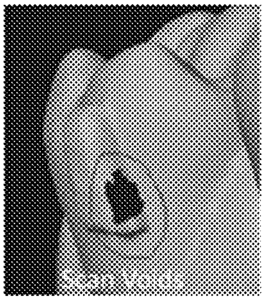

FIGS. 7A-7L are dental scans showing examples of existing attachments that may be determined not to have acceptable quality for activation. The attachments may 'fail' an attachment quality check. In these cases, the attachments may have been determined to have defects of different types that render them of unacceptable quality for activation. FIG. 7A shows an attachment that may be too narrow to provide a sufficient engagement surface area. FIGS. 7B, 7C, and 7D each show an attachment that may be too shallow or flat to provide a sufficient engagement surface area. FIG. 7D may, for example, be a button attachment. FIG. 7E shows an attachment that may be too misshapen to provide a sufficient engagement surface area. FIG. 7F shows an underlying tooth surface having flash, which may render the attachment unsuitable for engagement with a dental appliance. FIG. 7G shows an attachment that appears pitted, which may be due to a scan error. FIGS. 7I-7L each show scans with defects that may be due to scanning errors.

Figure 8A:
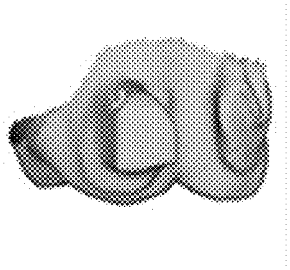
FIGS. 8A-8I illustrate examples of dental showing examples of existing attachments and illustrating identified engagement surfaces.
Figure 8B:
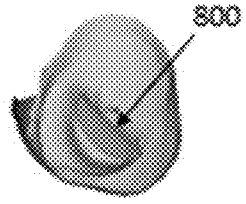
Figure 8C:
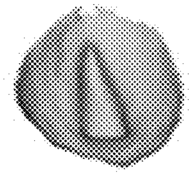
Figure 8D:
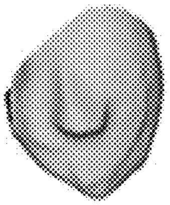
Figure 8E:
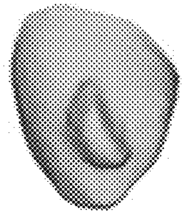
Figure 8F:
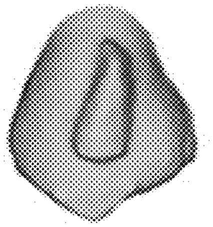
Figure 8G:
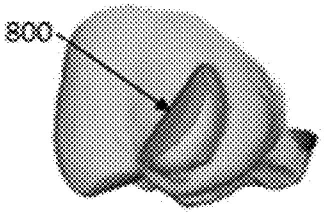
Figure 8H:
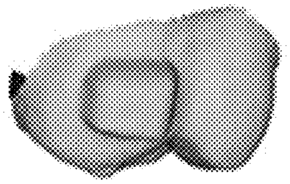
Figure 8I:
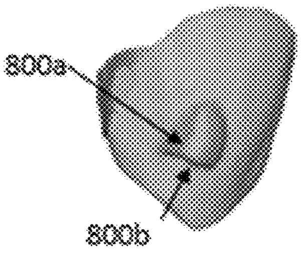

FIGS. 8A-8I are dental scans of teeth with existing attachments illustrating examples of how engagement surfaces may be identified. FIGS. 8A-8D show dental scans of molded attachments, such as described above with respect to FIG. 5B. FIGS. 8E-8H show dental scans of preformed attachments, such as described above with respect to FIG. 5C. In each of these examples of FIGS. 8A-8I, at least one qualified plane for activation is identified on the attachments. See, e.g., qualified planes for activations 800. In some cases, multiple planes of qualified planes for activation are identified. For example, FIG. 8I shows two qualified planes for activation 800*a* and 800*b*. In some cases, multiple planes of activation are presented due to in vivo wear (formed while the patient has the attachment on their teeth).

Figure 9A:
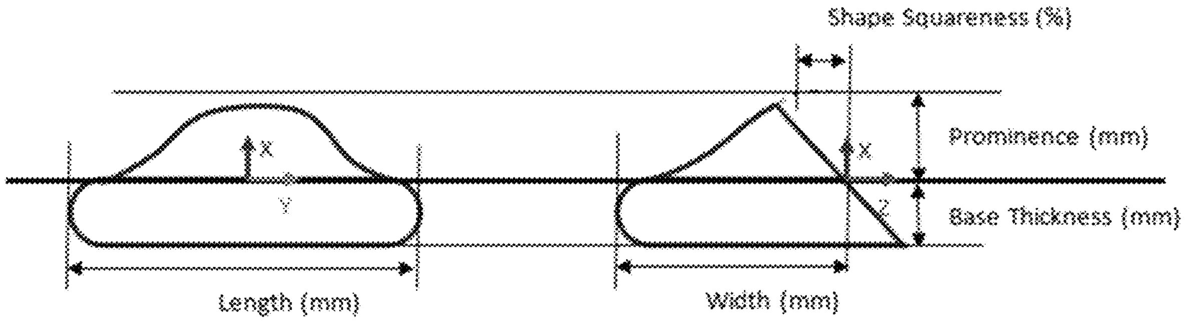
FIGS. 9A-9C illustrate an example of applying an offset for a dental appliance and providing contact relief on non-active surfaces of an existing attachment.
Figure 9B:
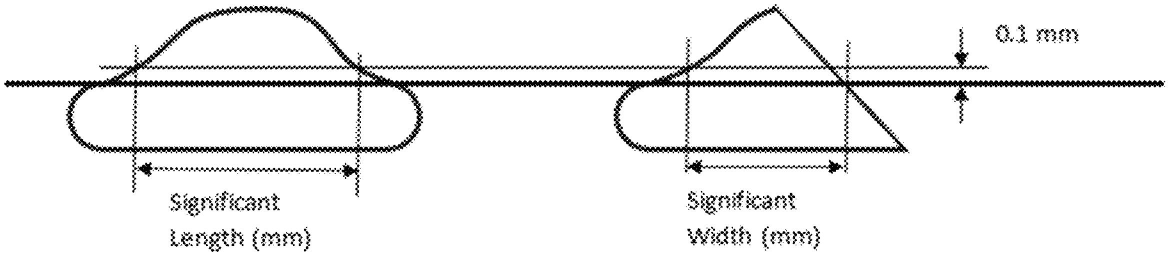
Figure 9C:
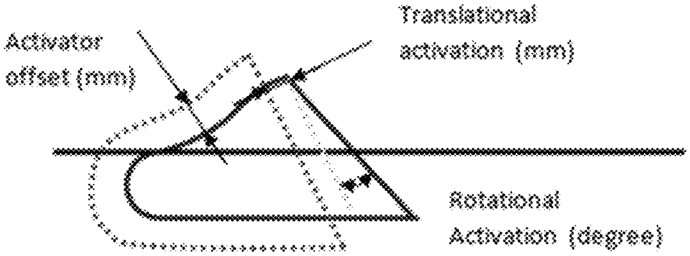

FIGS. 9A-9C illustrate an example of applying an offset for a dental appliance and providing contact relief on non-active surfaces of an existing attachment. FIG. 9A shows a length and a width of an attachment, as well as an example determination of a base thickness, prominence, and shape squareness of the attachment. FIG. 9B shows an example of how a significant length and significant width of the attachment may be determined based on the length, width, base thickness, prominence, and shape squareness of the attachment. The attachment has an activated dental appliance engagement surface that is configured to engage with a dental appliance in a manner that that applies a repositioning force against a tooth in which the attachment is bonded.

FIG. 9C shows example dimensions of an attachment cavity (also referred to as a 'pocket') of a dental appliance with respect to the attachment. An attachment engagement surface of the attachment cavity has dimensions that are offset (activator offset) with respect to the dimensions of the dental appliance engagement surface of the attachment, thereby providing the repositioning force. In this case, the attachment cavity is configured to apply rotational activation along: the horizontal axis on top of the attachment active surface; and the vertical axis on bottom right of the left corner of the active surface.

Figure 10:
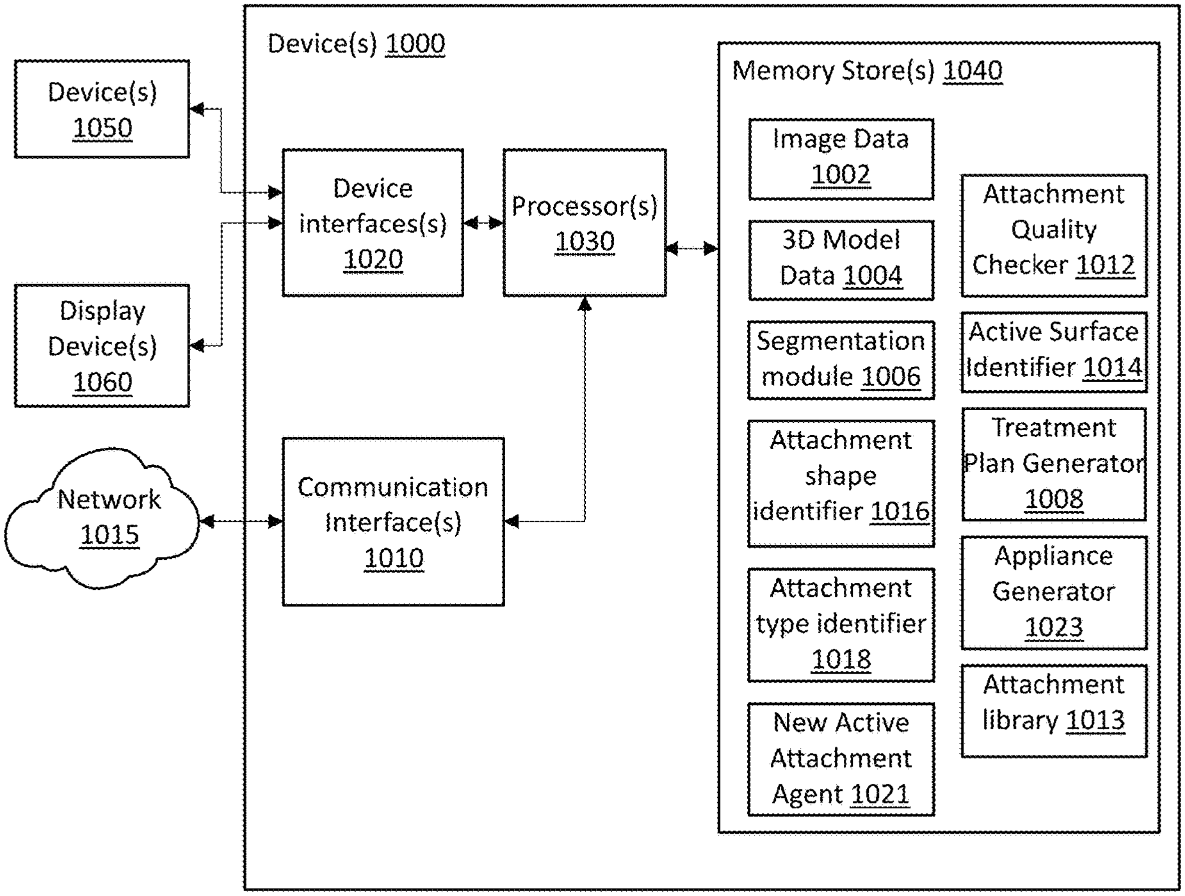
FIG. 10 illustrates an example block diagram of an example system that includes one or more devices for implementing one or more of the methods described herein.

FIG. 10 shows an example system that includes one or more devices 1000 for implementing one or more of the methods described herein. Although described herein as a device, the functionality of the device 1000 may be performed by any feasible apparatus, system, or method. In one example, the device 1000 may include one or more computer servers that are configured to generate one or more orthodontic treatment plans. The computer server(s) may be configured to communicate with one or more device(s) 1050, which may include one or more client computer(s), for example, at a dentist's office. The client computer(s) may include client software for interfacing with the computer server(s).

The device 1000 may include one or more communication interfaces 1010, one or more device interfaces 1020, one or more processors 1030, and one or more memory stores 1040. In some examples, the device 1000 may be configured to analyze images (e.g., dental images) and generate output resulting from the analysis. For example, the device 1000 may be configured to receive a scan (e.g., including one or more images) of a subject's dentition and generate a digital model (e.g., 3D digital model) of the subject's dentition based on the scan.

The communication interface 1010, which may be coupled to a network 1015 and to the processor(s) 1030, may transmit signals to and receive signals from other wired or wireless devices, including remote (e.g., cloud-based) computing devices, storage devices, cameras, and/or displays. For example, the communication interface 1010 may include wired (e.g., serial, ethernet, or the like) and/or wireless (Bluetooth, Wi-Fi, cellular, or the like) transceivers that may communicate with any other feasible device through any feasible network 1015.

The device interface 1020, which is coupled to the processor 1030, may be used to interface with any feasible input and/or output device. The device(s) 1050 may include one or more image capturing devices. Example image capturing devices may include intraoral scanners, optical cameras, x-ray devices, panoramic x-ray devices, portable cameras (e.g., phone cameras), and/or other imaging devices. In some examples, the device interface 1020 may be coupled to an interface with one or more display devices 1060. The display device(s) 1060 may be part of or separate from the device(s) 1050. In some examples, the device(s) 1050 may include one or more fabrication devices. Example fabrication devices may include one or more 3D printers, molding devices, and/or other manufacturing devices. Through the display device 1060 (e.g., computer monitor), the processor (s) 1030 may display images, feedback information, instructions, or other information (e.g., to a user).

In some examples, an image capturing device of the device(s) 1050 and/or the display device 1060 may be an integral part of the device 1000, or a portion of the device 1000. In other words, the image capturing device 1050 and/or the display device 1060 may share a common housing or enclosure. In some examples, the image capturing device of the device(s) 1050 and/or the display device 1060 are physically separate from the device 1000.

The processor(s) 1030, which is/are coupled to the memory store(s) 1040, may be any one or more suitable processors capable of executing scripts or instructions of one or more software programs stored in the device 1000 (such as within the memory store(s) 1040). The memory store(s) 1040 may include a non-transitory computer-readable storage medium (e.g., one or more nonvolatile memory elements, such as EPROM, EEPROM, Flash memory, a hard drive, etc.).

The memory store(s) 1040 may include image data 1002. The image data 1002 may include one or more images (e.g., 2D and/or 3D images), for example, captured by the one or more imaging capturing devices 1050. For example, the image data 1002 may be obtained through the communication interface 1010 and stored within the memory store(s) 1040. The image data 1002 may include images (e.g., scans) including optical images, x-ray images, panoramic images, video images, video frames, composite images formed from two or more source images, and/or other types of images. In some cases, the image data 1002 may include segmented data, in which boundaries of objects (e.g., teeth and/or gums) are identified and labeled (e.g., on a pixel-by-pixel basis). In some examples, the processor 1030 is configured to segment an unsegmented image.

The memory store(s) 1040 may include 3D model data 1004. The 3D model data 1004 may include one or more digital 3D models each represented as a mesh. For example, the 3D model data 1004 may include a series of digital 3D models represented as a series of meshes corresponding to different stages of a treatment plan for a patient. One or more treatment plans may be generated by a treatment plan generator 1008 that is executable by the processor 1030. In some cases, the 3D models may be segmented such that boundaries of objects (e.g., teeth and/or gums) are identified and labeled by a segmentation module 1006. The processor may be configured to analyze the 3D models prior to and/or after segmentation. In some examples, the 3D models are imported (e.g., via the communication interface 1010) as pre-segmented meshes. In other examples, the processor(s) 1030 is configured to generate the 3D models. For example, the processor 1030 may be configured to generate meshes from 3D image data, for example, from the image data 1002 (e.g., from a scan of a patient's teeth). In some examples, the 3D model is generated based on images of the patient's teeth with existing attachments already on the teeth.

An attachment shape identifier 1016 can be configured to determine a shape of the existing attachment. For example, the shape identifier 1016 may be configured to compare a current scan (e.g., current 3D model based on the current scan) with a prior scan (e.g., prior 3D model based on the prior scan). In some cases, the comparison includes subtracting out a tooth shape in the current scan, leaving the shape of the existing attachment on the tooth.

An attachment type identifier 1018 can be configured to identify the type of the existing attachment. In some examples, the identification is made automatically. In some examples, the existing attachment may be identified as being a preformed attachment (formed prior to placement on the teeth), molded attachments (formed from a template), or other (e.g., uncertain). The attachment identifier 1018 may be configured to recognize the attachment type based on comparing the shape and/or other attributes (e.g., color) of the existing attachment with attributes of other attachments, e.g., from an attachment library 1013. Factors may include whether the attachment is used to apply a translation, a rotation, an intrusion, or an extrusion force to a tooth. In some examples, the comparison and identification may be made using a machine learning agent that is trained on attachments having different shapes and/or attributes, e.g., from the attachment library 1013 and/or other data sources. If attachment type is not able to be identified, the attachment type identifier 1018 may be configured to generate a message to inform the user. The attachment identifier 1018 may be configured to determine that the scan data is not sufficient to make the identification and to recommend that another scan be taken.

An attachment quality checker 1012 can be configured to assess whether the existing attachment is of sufficient quality to be activated. In some examples, the quality check is made automatically. The attachment quality checker 1012 may be configured to identify regions of the existing attachment that could engage with the dental appliance to apply repositioning forces as distinct over other types of forces (e.g., buttons, power arms, bite-ramps, or other appliances: e.g. distalizers). The quality assessment can include determining whether the existing attachment has flat planes, sufficient volume or mass, missing an attachment material, and/or voids/air-bubbles. The quality assessment can include determining whether the scan data is not sufficient due to scan errors (e.g. visible pitting, holes, and/or stitching errors), and/or does the underlying tooth surface have flash. Attachments having an 'uncertain' quality may be marked for virtual removal. The quality may be assessed based on a quality threshold in which attachments with quality values at or above the threshold 'pass' and attachments with quality values less than the threshold 'fail'.

An active surface identifier 1014 can be configured to determine whether an existing attachment has any potential planes of activation for implementation in the secondary treatment plan. If the existing attachment has already passed a quality check (e.g., using attachment quality checker 1012), the active surface identifier 1014 can be used to determine if the existing attachment should be used as an active attachment or a passive attachment in the secondary treatment plan. The selection of active versus passive attachment may be based on whether the existing attachment has potential planes of activation for accomplishing desired tooth movement. If it is determined that the existing attachment does have potential planes of activation, the existing attachment can be marked as an active attachment. In some cases, a segmentation step (e.g., auto-segmentation) is applied to segment the existing attachment as an active attachment. If it is determined that the existing attachment does not have potential planes of activation, the existing attachment can be marked as a passive attachment.

Once the existing attachment is identified as active or passive, this information can be used as an input for the treatment plan generator 1008 to generate the secondary treatment plan for the remaining tooth movement. For example, the treatment plan generator 1008 can be configured to apply the appropriate offset(s) to a dental appliance where the dental appliance contacts the active attachments plane(s) of the active attachment. In the case of a passive attachment, the treatment plan generator 1008 can provide a dental appliance that uses the passive attachment passively, such as an anchor.

In cases where the existing attachment is removed (e.g., due to poor quality or it not being appropriate attachment), a new active attachment agent 1021 may optionally be used to determine whether one or more new active attachments should be added (e.g., to replace the removed existing attachment). The treatment plan generator 1008 can then be used to generate one or more treatment plans with the new active attachment(s).

An appliance generator 1023 may be configured to generate one or more dental appliances based on the one or more treatment plans. The dental appliance(s) may be virtual dental appliance(s). The virtual appliance(s) may be shaped to apply forces on the one or more active attachments bonded on the patient's teeth in directions and with magnitudes according to the treatment plan(s). For example, a set of appliances may be generated, where each virtual appliance is configured to implement a stage of a treatment plan. The appliance(s) may be in a format that is capable of being read by a fabrication device (e.g., device 1050) to produce one or more physical dental appliances.

Systems

In general, these methods and apparatuses may be used at one or more parts of a dental computing environment, including as part of an intraoral scanning system, doctor system, treatment planning system, patient system, and/or fabrication system. In particular, these methods and apparatuses may be used as part of a treatment planning system, for example, to generate and/or modify one or more treatment plans, and/or for generating one or more dental appliances to perform the treatment plan.

Figure 11:
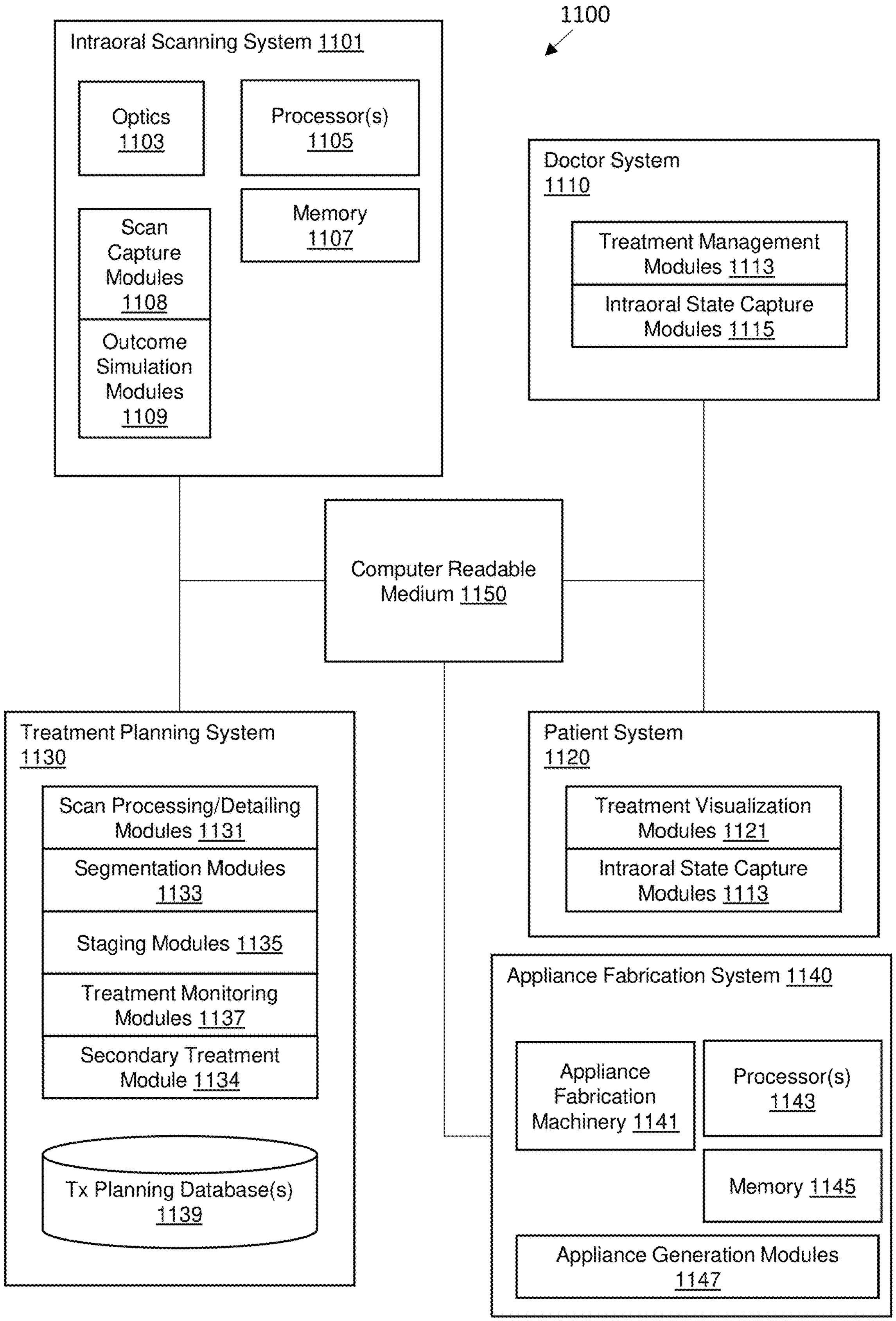
FIG. 11 is a diagram of one example of a computing environment within which the methods and apparatuses described herein may be implemented.

For example, FIG. 11 is a diagram illustrating one variation of a computing environment 1100 that may generate one or more orthodontic treatment plans specific to a patient and fabricate dental appliances that may accomplish the treatment plan to treat a patient, under the direction of a dental professional, using the activated attachments described herein. The example computing environment 1100 shown in FIG. 11 may include an intraoral scanning system 1101, a doctor system 1110, a treatment planning system 1130 (e.g., technician system), a patient system 1120, an appliance fabrication system 1140, and computer-readable medium 1150. In some variations a computing environment (dental computing system) 1100 may include just one or a subset of these systems (which may also be referred to as sub-systems of the overall system 1100). Further, one or more of these systems may be combined or integrated with one or more of the other systems (sub-systems), such as, e.g., the patient system and the doctor system may be part of a remote server accessible by doctor and/or patient interfaces. The computer readable medium 1150 may be divided between all or some of the systems (subsystems). For example, the treatment planning system 1130 and appliance fabrication system 1140 may be part of the same sub-system and may be on a computer readable medium 1150. Further, each of these systems may be further divided into sub-systems or components that may be physically distributed (e.g., between local and remote processors, etc.) or may be integrated.

The intraoral scanning system 1101 may include an intraoral scanner as well as one or more processors for processing images. For example, an intraoral scanning system 1101 can include optics 1103 (e.g., lens(es), filters, light sources, etc.), processor(s) 1105, a memory 1107, scan capture modules 1108, and outcome simulation modules 1109. In general, the intraoral scanning system 1101 can capture one or more images of a patient's dentition. Use of the intraoral scanning system 1101 may be in a clinical setting (doctor's office or the like) or in a patient-selected setting (the patient's home, for example). In some cases, operations of the intraoral scanning system 1101 may be performed by an intraoral scanner, dental camera, cell phone or any other feasible device.

Any of the component systems or sub-systems of the dental computing environment 1100 may access or use the methods and apparatuses described herein. For example, the doctor system 1110 may include treatment management modules 1113 and intraoral state capture modules 1115 that may access or use both the 3D model of the patient's dentition and one or more digital models of the prefabricated attachments. The doctor system 1110 may provide a "doctor facing" interface to the computing environment 1100. The treatment management modules 1113 can perform any operations that enable a doctor or other clinician to manage the treatment of any patient. In some examples, the treatment management modules 1113 may provide a visualization and/or simulation of the patient's dentition with respect to a treatment plan. In some examples, the treatment management modules 1113 can enable the doctor to modify or revise a treatment plan, particularly when images provided by the intraoral state capture modules 1115 indicate that the movement of the patient's teeth may not be according to the treatment plan. The doctor system 1110 may include one or more processors configured to execute any feasible non-transitory computer-readable instructions to perform any feasible operations described herein.

The doctor system 1110 may allow the doctor to request whether any existing attachments on a patient's teeth may be activated in a secondary treatment plan. For example, the treatment management module 1113 may include a user interface for the doctor that allows the doctor to interactively communicate with a secondary treatment module 1134 of the treatment planning system 1130. The doctor may submit a current scan of the patient's teeth with existing attachments on the patient's teeth. The scan may be captured using one or more intraoral state capture modules 1115. The doctor may also submit one or more prior scans of the patient's teeth, for example, with or without the attachments on the teeth. The doctor may also submit a 3D model of the patient's dentition in a final desired tooth configuration resulting from the secondary treatment. Such 3D model may be formed using the treatment management module 1113.

The secondary treatment module 1134 is configured to determine whether any of the existing attachments could be actively used in the secondary treatment and transmit associated information back to the doctor system 1110. For example, the secondary treatment module 1134 may transmit to the doctor system 1110 whether any of the existing attachments should be removed, any of the existing attachments may be used as active attachments in the secondary treatment plan, and/or any of the existing attachments may be used as passive attachments in the secondary treatment plan. The secondary treatment module 1134 can also be configured to calculation one or more secondary treatment plans with any confirmed active attachments and/or passive attachments integrated therein.

The treatment planning system 1130 may include any of the methods and apparatuses described herein. The treatment planning system 1130 may include scan processing/detailing modules 1131, segmentation modules 1133, staging modules 1135, treatment monitoring modules 1137, and treatment planning database(s) 1139. In general, the treatment planning system 1130 can determine a treatment plan for any feasible patient. The scan processing/detailing modules 1131 can receive or obtain dental scans (such as scans from the intraoral scanning system 1101) and can process the scans to remove scan errors and, in some cases, enhancing details of the scanned image.

A treatment planning system 1130 may include a segmentation module 1133 that can segment a dental model into separate parts including separate teeth, gums, jaw bones, attachments, and the like. The staging modules 1135 may determine different stages of a treatment plan. Each stage may correspond to a different dental appliance and may use the same or different attachments. The staging modules 1135 may also determine the final position of the patient's teeth, in accordance with a treatment plan. Thus, the staging modules 1135 can determine some or all of a patient's orthodontic treatment plan. In some examples, the staging modules can simulate movement of a patient's teeth in accordance with the different stages of the patient's treatment plan using the determined attachments.

The treatment monitoring modules 1137 can monitor the progress of an orthodontic treatment plan. In some examples, the treatment monitoring modules can provide an analysis of progress of treatment plans to a clinician. The orthodontic treatment plans may be stored in the treatment planning database(s) 1139. Although not shown, the treatment planning system 1130 can include one or more processors configured to execute any feasible non-transitory computer-readable instructions to perform any feasible operations described herein.

The patient system 1120 can include treatment visualization modules 1121 and intraoral state capture modules 1115. In general, the patient system can provide a "patient facing" interface to the computing environment 1100. The treatment visualization modules 1121 can enable the patient to visualize how an orthodontic treatment plan has progressed and also visualize a predicted outcome (e.g., a final position of teeth). In some examples, the patient system 1120 can capture dentition scans for the treatment visualization modules 1121 through the intraoral state capture modules 1123. The intraoral state capture modules can enable a patient to capture his or her own dentition through the intraoral scanning system 1101. Although not shown here, the patient system 1120 can include one or more processors configured to execute any feasible non-transitory computer-readable instructions to perform any feasible operations described herein.

The appliance fabrication system 1140 can include appliance fabrication machinery 1141, processor(s) 1143, memory 1145, and appliance generation modules 1147. In general, the appliance fabrication system 1120 can directly or indirectly fabricate dental appliances to implement an orthodontic treatment plan. In some examples, the orthodontic treatment plan may be stored in the treatment planning database(s) 1139.

The appliance fabrication machinery 1141 may include any feasible implement or apparatus that can fabricate any suitable dental appliance. The appliance generation modules 1147 may include any non-transitory computer-readable instructions that, when executed by the processor(s), can direct the appliance fabrication machinery 1141 to produce one or more dental appliances. The memory 1145 may store data or instructions for use by the processor(s) 1143. In some examples, the memory 1145 may temporarily store a treatment plan, dental models, or intraoral scans.

The computer-readable medium 1150 may include some or all of the elements described herein with respect to the computing environment 1100. The computer-readable medium 1150 may include non-transitory computer-readable instructions that, when executed by a processor, can provide the functionality of any device, machine, or module described herein.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for secondary orthodontic treatment planning, the method comprising:
- receiving a scan of a subject's dentition including an existing attachment on the subject's dentition;
- determining a shape of the existing attachment based on comparing the scan to one or more prior scans of the subject's dentition;
- determining that the existing attachment is suitable for activation to achieve one or more tooth movements, at least partially based on the shape of the existing attachment;
- identify a dental appliance engagement surface of the existing attachment when the attachment is suitable for activation;
- generating a secondary treatment plan including applying a force to the subject's dentition via the identified dental appliance engagement surface; and
- generating a dental appliance that accommodates the existing attachment based on the secondary treatment plan.

2. The method of claim 1, further comprising confirming that a total number of the attachments for the secondary treatment plan is less than or equal to a user's preference for a preferred total number of attachments.

3. The method of claim 1, wherein determining that the existing attachment is suitable for activation comprises determining that the existing attachment has one or more potential planes of activation that are suitable for implementing the secondary treatment plan.

4. The method of claim 3, wherein determining that the existing attachment has one or more potential planes of activation includes determining that the existing attachment includes a surface having at least a minimum area.

5. The method of claim 1, wherein generating the dental appliance comprises generating one or more digital models of the dental appliance.

6. The method of claim 1, wherein the current scan and the one or more prior scans include one or more of: an intraoral scan, a cone beam computed tomography (CBCT) scan, and an x-ray.

7. The method of claim 1, wherein determining that the existing attachment is suitable for activation further comprises:
- identifying a type of the existing attachment as a molded attachment, a preformed attachment or uncertain; and
- determining whether the identified type of the existing attachment is usable as an active attachment.

8. The method of claim 7, wherein identifying the type of the existing attachment includes using a trained machine learning agent.

9. The method of claim 1, wherein determining that the existing attachment is suitable for activation further comprises determining that the engagement surface is suitably positioned and oriented with respect to the tooth according to an intended movement of the tooth to be implemented in the secondary treatment plan.

10. The method of claim 1, wherein determining that the existing attachment is suitable for activation to achieve one or more tooth movements includes determining whether the one or more existing attachments is pitted, cracked, has poor surface quality, has poor bond quality, and/or is not appropriately oriented for an intended movement of a corresponding tooth.

11. The method of claim 1, further comprising removing the existing attachment from the secondary treatment plan if the existing attachment is not suitable for activation to achieve one or more intended movement of the tooth to be implemented in the secondary treatment plan.

12. The method of claim 1, wherein the dental appliance includes an aligner and/or a palatal expander.

13. The method of claim 1, further comprising a series of dental appliances that are shaped to move the subject's teeth incrementally according to the secondary treatment plan.

14. The method of claim 1, wherein the existing attachment includes a dental attachment bonded to the subject's teeth and used in prior treatment plan.

15. The method of claim 1, wherein the existing attachment is a preformed attachment that is categorized according to a library of dental attachments.

16. The method of claim 1, wherein the existing attachment is a natural feature on the subject's tooth, wherein the natural feature includes a protrusion or a ridge on the subject's tooth.

17. The method of claim 1, further comprising confirming that a user would like to use the existing attachment in the secondary treatment plan.

18. The method of claim 1, further comprising repeating the steps of determining the shape, determining that the existing attachment is suitable, and activating the dental appliance engagement surface for multiple existing attachments on the subject's dentition.

19. A system for secondary orthodontic treatment planning, the system comprising:
- one or more processors; and
- one or more memory stores coupled to one or more processors, the one or more memory stores configured to store computer instructions that, when executed by the one or more processors, perform a computer-implemented method comprising:
  - receiving a scan of a subject's dentition including an existing attachment on the subject's dentition;
  - determining a shape of the existing attachment based on comparing the scan to one or more prior scans of the subject's dentition;
  - determining that the existing attachment is suitable for activation to achieve one or more tooth movements, at least partially based on the shape of the existing attachment;
  - identify a dental appliance engagement surface of the existing attachment when the attachment is suitable for activation;
  - generating a secondary treatment plan including applying a force to the subject's dentition via the identified dental appliance engagement surface; and
  - generating a dental appliance that accommodates the existing attachment based on the secondary treatment plan.

20. A method for secondary orthodontic treatment planning, the method comprising:
- receiving, from a user, a request to use an existing attachment on a subject's dentition in a secondary treatment plan;
- sending, to a treatment planning system, a current scan of the subject's dentition including the existing attachment on the subject's dentition;
- receiving, from the treatment planning system, an indication that the existing attachment is determined to be suitable for activation, wherein the determination is at least partially based on one or more quality assessment criteria based on a shape of the existing attachment;

sending, to the treatment planning system, a confirmation accepting use of the existing attachment as an active attachment in the secondary treatment plan; and receiving a dental appliance including an attachment engagement surface that is offset with respect to a dental appliance engagement surface of the existing attachment so that the dental appliance can apply the force on the subject's dentition.

* * * * *